United States Patent
Li et al.

(10) Patent No.: US 9,249,172 B2
(45) Date of Patent: Feb. 2, 2016

(54) PYRAZOLE DERIVATIVES

(75) Inventors: Chenxi Li, Suzhou (CN); Weisheng Shen, Suzhou (CN); Yang Fang, Suzhou (CN); Xiaoyong Le, Suzhou (CN)

(73) Assignees: HANDE PHARMA LIMITED, Suzhou, Jiangsu Province (CN); HANDE STARLAKE BIOSCIENXE CO., LTD., Suzou, Jiangsu Province (CN)

(*) Notice: Subject to any disclaimer, the term of this patent is extended or adjusted under 35 U.S.C. 154(b) by 395 days.

(21) Appl. No.: 13/698,548

(22) PCT Filed: May 23, 2011

(86) PCT No.: PCT/CN2011/074519
§ 371 (c)(1),
(2), (4) Date: Feb. 19, 2013

(87) PCT Pub. No.: WO2011/147296
PCT Pub. Date: Dec. 1, 2011

(65) Prior Publication Data
US 2013/0142757 A1 Jun. 6, 2013

(30) Foreign Application Priority Data
May 24, 2010 (CN) .......................... 2010 1 0180845

(51) Int. Cl.
| | |
|---|---|
| A61K 45/00 | (2006.01) |
| A61K 38/21 | (2006.01) |
| A61K 38/46 | (2006.01) |
| A61K 39/00 | (2006.01) |
| C12N 9/99 | (2006.01) |
| C07H 17/02 | (2006.01) |
| A61K 38/14 | (2006.01) |
| A61K 38/12 | (2006.01) |
| A61K 38/07 | (2006.01) |
| A61K 31/70 | (2006.01) |
| A01N 43/04 | (2006.01) |
| C07D 487/04 | (2006.01) |
| A61K 31/706 | (2006.01) |
| A61K 45/06 | (2006.01) |
| C07D 471/04 | (2006.01) |

(52) U.S. Cl.
CPC .............. *C07H 17/02* (2013.01); *A61K 31/706* (2013.01); *A61K 45/06* (2013.01); *C07D 471/04* (2013.01); *C07D 487/04* (2013.01)

(58) Field of Classification Search
CPC .... C07D 487/04; C07D 471/04; C07H 17/02; A61K 31/706; A61K 45/06; A61K 2300/00
See application file for complete search history.

(56) References Cited

U.S. PATENT DOCUMENTS

| | | | |
|---|---|---|---|
| 6,541,484 B2 | 4/2003 | Collins et al. | |
| 8,546,368 B2* | 10/2013 | Penning et al. | 514/183 |
| 2007/0032515 A1 | 2/2007 | Anand et al. | |
| 2010/0113415 A1 | 5/2010 | Rajapakse et al. | |

FOREIGN PATENT DOCUMENTS

| | | |
|---|---|---|
| CN | 101421268 A | 4/2009 |
| WO | 2007095628 A1 | 8/2007 |

OTHER PUBLICATIONS

International Search Report issued in International Patent Application No. PCT/CN2011/074519 mailed Sep. 1, 2011.
Kummar, S. et al., "A Phase I Study of Veliparib in Combination with Metronomic Cyclophosphamide in Adults with Refractory Solid Tumors and Lymphomas," Clin. Cancer Res., Mar. 15, 2012; vol. 18(6), pp. 1726-1734.
Albert, J. M. et al., "Inhibition of Poly(ADP-Ribose) Polymerase Enhances Cell Death and ImprovesTunnor Growth Delay in Irradiated Lung Cancer Models," Clin. Cancer Res., 2007, vol. 13(10), pp. 3033-3042.
Plummer, R. et al., "Phase I Study of the Poly(ADP-Ribose) Polymerase Inhibitor, AG014699, in Combination with Temozolomide in Patients with Advanced Solid Tumors," Clin. Cancer Res., 2008, vol. 14, pp. 7917-7923.
Lee, J. J. et al., "Combining poly(ADP-ribose) polymerase 1 (PARP-1) inhibition and radiation in Ewing sarcoma results in lethal DNA damage," Mol. Cancer Ther., 2013, vol. 12(11), pp. 1-16.

(Continued)

*Primary Examiner* — Lawrence E Crane
(74) *Attorney, Agent, or Firm* — Ping Wang; Andrews Kurth LLP

(57) ABSTRACT

Disclosed are pyrazole compounds of general formula (I), wherein R, $R_1$, $R_c$, $R_d$, $R_e$, $R_f$, X, Y, Z, A and B are as defined in the application. These compounds are active as inhibitors of poly(ADP-ribose)polymerase (PARP) and are useful in methods for treating diseases or conditions mediated by PARP, including breast cancer and malignant melanoma.

general formula (I)

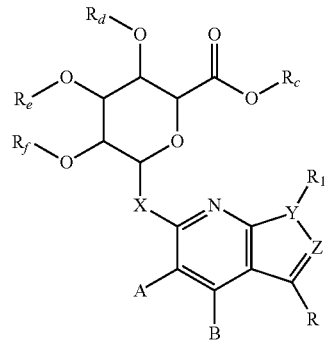

17 Claims, No Drawings

(56) References Cited

OTHER PUBLICATIONS

Passaro, C. et al., "PARP inhibitor olaparib increases the oncolytic activity of dl922-947 in in vitro and in vivo model of anaplastic thyroid carcinoma," Molecular Oncology, 2015, vol. 9, pp. 78-92.

Norris, R. E. et al., "Preclinical Evaluation of the PARP Inhibitor, Olaparib, in Combination with Cytotoxic Chemotherapy in Pediatric Solid Tumors," Pediatr. Blood Cancer, 2014, vol. 61(1), pp. 1-15.

Min, A. et al., "RAD51C-Deficient Cancer Cells Are Highly Sensitive to the PARP Inhibitor Olaparib," Mol. Cancer Ther., 2013, vol. 12, pp. 865-877.

Bridges, K. A. et al., "Niraparib (MK-4827), a novel poly(ADP-Ribose) polymerase inhibitor, radiosensitizes human lung and breast cancer cells," Oncotarget, 2014, vol. 5(13), pp. 5076-5086.

Genther Williams, S. M. et al., "Treatment with the PARP inhibitor, niraparib, sensitizes colorectal cancer cell lines to irinotecan regardless of MSI/MSS status," Cancer Cell International, 2015, vol. 15(14), pp. 2-11.

Shen, Y. et al., "BMN673, a Novel and Highly Potent PARP1/2 Inhibitor for the Treatment of Human Cancers with DNA Repair Deficiency," Clin. Cancer Res., 2013, vol. 19:, pp. 5003-5015.

Sonnenblick, A. et al., "An update on PARP inhibitors-moving to the adjuvant setting," Nat. Rev. Clin. Oncol., 2015, vol. 12, pp. 27-41.

Chuang, H. C. et al., "Differential anti-proliferative activities of poly(ADP-ribose) polymerase (PARP) inhibitors in triple-negative breast cancer cells," Breast Cancer Res. Treat., Jul. 2012, vol. 134(2), pp. 649-659.

Yuan, Y. et al., "Novel targeted therapeutics: inhibitors of MDM2," Journal of Hematology & Oncology, 2011, vol. 4 (16), pp. 1-14.

Ekblad et al., "PARP inhibitors: polypharmacology versus selective inhibition," The FEBS Journal, 2013, vol. 280, pp. 3563-3575.

Tangutooria, S. et al., "PARP inhibitors: A new era of targeted therapy," Maturitas, 2015, pp. 1-5.

Anwar, M. et al., "PARP inhibitors," Hereditary Cancer in Clinical Practice, 2015, pp. 1-4.

Sandhu, S. K. et al., "Poly(ADP-ribose) polymerase inhibitors in cancer treatment: A clinical perspective," European Journal of Cancer, 2010, vol. 46, pp. 9-20.

Reinbolt R. E. et al., "The role of PARP inhibitors in the treatment of gynecologic malignancies," Frontiers in Oncology, 2013, vol. 3(237), pp. 1-11.

* cited by examiner

PYRAZOLE DERIVATIVES

CROSS-REFERENCE TO RELATED APPLICATIONS

This application claims priority of PCT/CN2011/074519 filed May 23, 2011 under 35 U.S.C. §371(c).

FIELD

The present application is directed to organic chemistry and pharmaceutical chemistry.

BACKGROUND

Poly(ADP-ribose)polymerase, PARP, is also known as poly(ADP-ribose) synthase (PARS) or poly(ADP-ribose) transferase (PADPRT) and is one of key nucleus enzyme families present in eukaryotic cells. Up to date, it has been confirmed that the PARP nucleus enzyme family has 18 members, in which the most abundant member of PARP-1 functions more than 90% of the ribose diphosphate polymerization.

The structure of another member of this family PARP-2 is most similar to that of PARP-1. Both structures comprise three regions: one region is a DNA binding and nucleic aid orientation region comprising two "zinc finger" structures, which recognizes the damages of DNA by the zinc finger structures; the second region is central self-modifying region comprising 15 highly conservative glutamic acid residues, which is considered as a target of ribosylation of poly(ADP-ribose); and the third region is C-terminated region comprising NAD bonding sites and catalytic sites for synthesizing poly(ADP-ribose). The content of PARP is quite abundant in cells of the human body, especially in immunocytes and germ cells. The poly ADP ribosylation occurs in many physiological processes, leading to multiple effects, which include chromatin degradation, DNA replication, repair of DNA, genes expressions, division and differentiation of cells and apoptosis.

PARP also modulates expressions of various proteins including NO synthetase which mediates inflammation at transcriptional level. PARP, as a sensor for damages of DNA single- or double-strands, plays an important role in response to damages of DNA. When the double- or single strands of DNA breaks due to the effects such as radiation, oxidant and alkylating drugs, the activity of PARP significantly increases. Once the PARP is activated, the PARP cuts NAD into nicotinamide and ADP ribose, and polymerizes the latter onto nuclear receptor proteins including histone, transcription factor and PARP to form an adenosine diphosphate ribose polymer (PAR) similar to nucleic acids. The formation of the polymer with highly negative charges results in static pulse between DNA and histone and loose of the structure of chromatin. It is advantageous for recombination of chromatin, repair of DNA and modulation of transcription. It results in invasion of DNA repair enzymes such as XRCC1, LIGHIII, and the like, which is a key step in mechanism of DNA repairing.

Poly(ADP-ribose)polymerase plays two major opposite roles in response to DNA damage: PARP is one important factor for cell survival and maintaining the chromosome stability; on the other hand, the excessive activation of this enzyme is one of the important cause for apoptosis. The main reason causing the contradictory resides in that the external stimulates (such as alkylating reagents, rays, oxidation and others) cause different levels of DNA damages. When the DNA is slightly damaged, PARP is activated and repairs the damaged portions. When the cells are significantly damaged, PARP is largely activated and consumes a large number of NAD and further exhausts ATP in cells, such that the cells are in the state of energy deficiency and suffer more and unrepairabe damages, which result in necrosis or apoptosis of cells.

SUMMARY

In one aspect, the present application is directed to a compound of general formula (I), a single stereoisomer thereof, or a mixture of stereoisomers, a pharmaceutically acceptable salt thereof, a prodrug thereof, or a metabolite thereof:

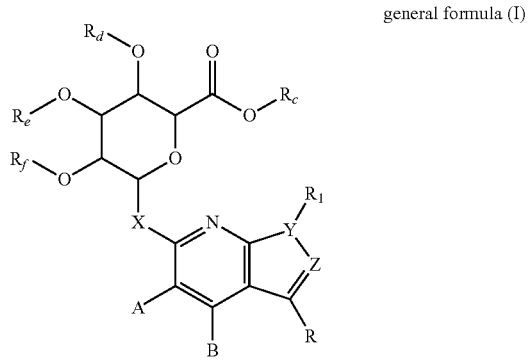

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of oxygen and sulphur; and

Y and Z are independently selected from the group consisting of nitrogen, oxygen, sulphur and optionally substituted methylene.

In another aspect, the present application is directed to a process for preparing a compound of general formula (I), comprising reacting a compound of general formula (XIV) and a compound of general formula (VI) to obtain the compound of general formula (I),

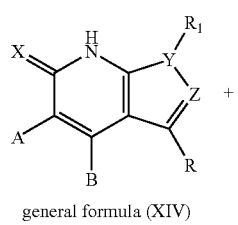

general formula (XIV)

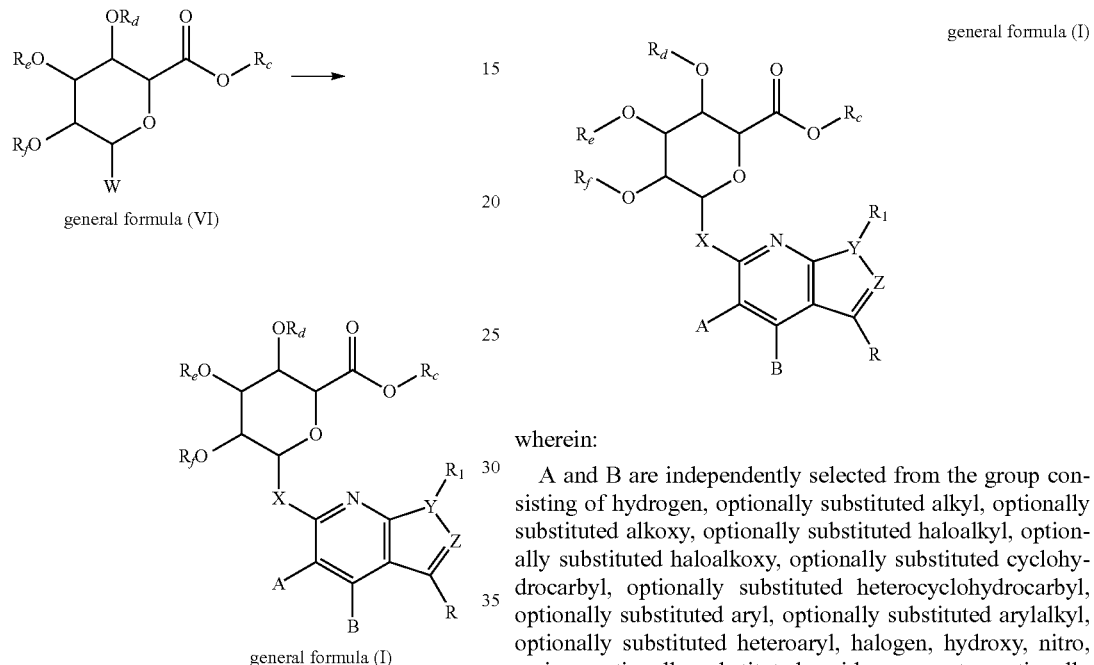

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

W is halogen;

X is selected from the group consisting of oxygen and sulphur; and

Y and Z are independently selected from the group consisting of nitrogen, oxygen, sulphur and optionally substituted methylene.

In still another aspect, the present application is directed to a pharmaceutical composition, comprising a pharmaceutically acceptable carrier and a therapeutically effective amount of a compound of general formula (I), a single stereoisomer thereof, or a mixture of stereoisomers, a pharmaceutically acceptable salt thereof, a prodrug thereof, or a metabolite thereof:

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of oxygen and sulphur; and

Y and Z are independently selected from the group consisting of nitrogen, oxygen, sulphur and optionally substituted methylene.

In yet another aspect, the present application is directed to a method for inhibiting activities of poly(ADP-ribose)polymerase (PARP), comprising contacting a therapeutically effective amount of a compound of general formula (I), a single stereoisomer thereof, or a mixture of stereoisomers, a pharmaceutically acceptable salt thereof, a prodrug thereof, or a metabolite thereof with PARP,

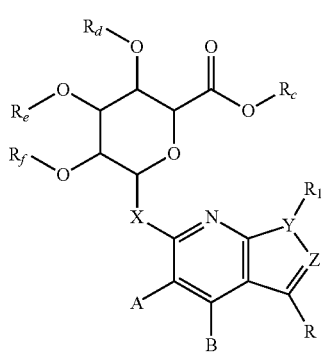

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of oxygen and sulphur; and

Y and Z are independently selected from the group consisting of nitrogen, oxygen, sulphur and optionally substituted methylene.

In still another aspect, the present application is directed to a method for treating diseases or conditions mediated by poly(ADP-ribose)polymerase (PARP), comprising administering a subject in need thereof a therapeutically effective amount of a compound of general formula (I), a single stereoisomer thereof, or a mixture of stereoisomers, a pharmaceutically acceptable salt thereof, a prodrug thereof, or a metabolite thereof,

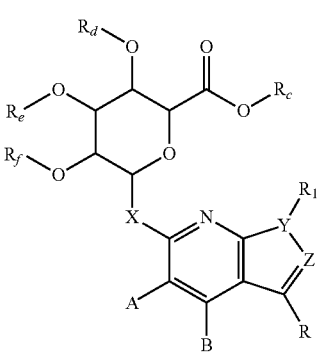

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B bond represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of oxygen and sulphur; and

Y and Z are independently selected from the group consisting of nitrogen, oxygen, sulphur and optionally substituted methylene.

DETAILED DESCRIPTION

In the following description, certain specific details are included to provide a thorough understanding of various disclosed embodiments. One skilled in the relevant art, however, will recognize that the embodiments may be practiced without one or more these specific details, or with other methods, components, materials, etc.

Unless the context required otherwise, throughout the specification and claims which follows, the term "comprise" and variation thereof, such as "comprises" and "comprising" are to be construed in an open, inclusive sense, which is as "include, but not limited to".

Reference throughout this specification to "one embodiment", or "an embodiment", or "in another embodiment", or "in some embodiments" means that a particular referent feature, structure or characteristic described in connection with the embodiment is included in at least one embodiment. Therefore, the appearance of the phrases "in one embodiment" or "in the embodiment" or "in another embodiment" or "in some embodiments" in various places throughout this specification are not necessarily all referring to the same embodiment. Moreover, the particular features, structures or characteristics may be combined in any suitable manner in one or more embodiments.

It should be noted that, as used in this specification and the appended claims, the singular forms "a", "an" and "the" include plural referents unless the context clearly stated otherwise. Therefore, for example, a reaction comprising "a catalyst" comprises one catalyst, two or more catalyst. It should be also noted that the use of "or" means "and/or" unless stated otherwise.

Definition

Certain chemical groups named herein are preceded by a shorthand notion indicating the total number of carbon atoms that are to be found in the indicated chemical groups. For example, $C_7$-$C_{12}$ alkyl describes an alkyl as defined below, having a total of 7 to 12 carbon atoms, and $C_4$-$C_{12}$ cyclohydrocarbylalkyl describes a cyclohydrocarbylalkyl, as defined below, having a total 4 to 12 carbon atoms. The total number of carbon atoms in the shorthand notation does not include carbons that may exist in the substituents of the groups described.

Accordingly, as used in the specification and appended claims, unless specified to the contrary, the following terms have the meanings indicated:

"Hydroxy" refers to the —OH group.
"Cyano" refers to the —CN group.
"Nitro" refers to the —$NO_2$ group.
"Amino" refers to the —$NH_2$ group.
"mercapto" refers to the —SH group.

"Alkyl" refers to a straight or branched hydrocarbon chain group consisting solely of carbon and hydrogen atoms, containing no unsaturation, having from one to twelve carbon atoms, preferably one to eight or one to six carbon atoms, and which is attached to the rest of the molecular by a single bond, e.g., methyl, ethyl, n-propyl, 1-methylethyl(isopropyl), n-butyl, n-pentyl, 1,1-dimethylethyl(t-butyl), and the like.

The alkyl group may be optionally substituted, i.e. substituted or unsubstituted. When substituted, the substituted group(s) is(are) individually and independently selected from cyclohydrocarbyl, aryl, heteroaryl, heteroalicyclic, hydroxy, hydrocarboxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof. Typical hydrocarbyl groups include, but are in no way limited to, methyl, ethyl, propyl, isopropyl, butyl, isobutyl, t-butyl, pentyl, hexyl, ethenyl, propenyl, buenyl, cyclopropyl, cyclobutyl, cyclopentyl, cyclohexyl, etc. Whenever a substituted is described as being "optionally substituted", that substituent may be substituted with one of the above substituents.

"Alkoxy" refers to a group of the formula —OR, where R is an alkyl group as defined above, e.g., methoxy, ethoxy, n-propoxy, 1-methylethoxy(isopropoxy), n-butoxy, iso-butoxy, sec-butoxy, t-butyoxy, amoxy, t-amoxy, and the like. The alkyl moiety of the alkoxy group can be optionally substituted, as defined for an alkyl group.

"Cyclohydrocarbyl" refers to a stable non-aromatic monocyclic or bicyclic hydrocarbon group consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, cyclodecyl, and the like.

Cyclohydrocarbyl group may be optionally substituted, i.e. substituted or unsubstituted. When substituted, the substituted group(s) is(are) individually and independently selected from cyclohydrocarbyl, aryl, heteroaryl, heteroalicyclic, hydroxy, hydrocarboxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof. Typical hydrocarbyl groups include, but are in no way limited to, methyl, ethyl, propyl, isopropyl, butyl, isobutyl, t-butyl, pentyl, hexyl, ethenyl, propenyl, buenyl, cyclopropyl, cyclobutyl, cyclopentyl, cyclohexyl, etc. Whenever a substituted is described as being "optionally substituted", that substituent may be substituted with one of the above substituents.

"Heterocyclyl" refers to a stable 3- to 18-membered non-aromatic ring group which consists of carbon atoms and from one to five heteroatoms selected from the group consisting of nitrogen, oxygen and sulphur. For the purpose of the present application, the heterocyclyl group can be a monocyclic, bicyclic, tricyclic or tetracyclic ring system, which may include fused or bridged ring systems. Moreover, the nitrogen, carbon or sulphur atoms in the heterocyclyl group can be optionally oxidized; the nitrogen atom can be optionally quaternized; and the heterocyclyl group can be partially or fully saturated. Examples of such heteroyclyl groups include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl.

Heterocyclyl group may be optionally substituted, i.e. substituted or unsubstituted. When substituted, the substituted group(s) is(are) individually and independently selected from cyclohydrocarbyl, aryl, heteroaryl, heteroalicyclic, hydroxy, hydrocarboxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof. Typical hydrocarbyl groups include, but are in no way limited to, methyl, ethyl, propyl, isopropyl, butyl, isobutyl, t-butyl, pentyl, hexyl, ethenyl, propenyl, buenyl, cyclopropyl, cyclobutyl, cyclopentyl, cyclohexyl, etc. Whenever a substituted is described as being "optionally substituted", that substituent may be substituted with one of the above substituents.

"Halo" refers to bromo, chloro, fluoro or iodo.

"Haloalkyl" refers to an alkyl, as defined above, that is substituted by one or more halo groups, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl group can be optionally substituted, as defined above for an alkyl group.

"Aryl" refers to aromatic monocyclic or multicyclic hydrocarbon ring system consisting only of hydrogen and carbon and containing from six to nineteen carbon atoms, preferably six to ten carbon atoms, where the ring system can be partially or fully saturated. Examples of an aryl group include, but are not limited to, fluorenyl, phenyl and naphthyl.

"Arylalkyl" refers to group of formula —$R_aR_b$, where $R_a$ is an alkyl as defined above, and $R_b$ is one or more aryl groups as defined above, e.g., benzyl, diphenylmethyl, and the like. The aryl part of the arylalkyl group can be optionally substituted, as defined above for an aryl group. The alkyl part of the heteroaryl group can be optionally substituted, as defined above for an alkyl group.

"Heteroaryl" refers to a 5- to 18-membered aromatic ring group which consists of carbon atoms and from one to five heteroatoms selected from the group consisting of nitrogen, oxygen and sulphur. For the purpose of the present application, the heteroaryl can be a monocyclic, bicyclic, tricyclic or tetracyclic ring system, which may include fused or bridged ring systems. Moreover, the nitrogen, carbon or sulphur atoms in the heteroaryl group can be optionally oxidized; the nitrogen atom can be optionally quaternized. Examples include, but are not limited to, azepinyl, acridinyl, benzimidazolyl, benzothiazolyl, benzoindolyl, benzothiadiazolyl, benzonaphthofuranyl, benzoxazolyl, benzodioxolyl, benzodioxinyl, benzopyranyl, benzopyronyl, benzofuranyl, benzofuranonyl, benzothienyl(benzothiophenyl), benzotriazolyl, benzo[4,6]imidazo[1,2-a]pyridyl, carbazolyl, cinnolinyl, dibenzofuranyl, furyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, 2,3-phthalazinonyl, pteridinyl, purinyl, pyrrolyl, pyrazolyl, pyridyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl and thiophenyl.

Heteroaryl group may be optionally substituted, i.e. substituted or unsubstituted. When substituted, the substituted group(s) is(are) individually and independently selected from cyclohydrocarbyl, aryl, heteroaryl, heteroalicyclic, hydroxy, hydrocarboxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof. Typical hydrocarbyl groups include, but are in no way limited to, methyl, ethyl, propyl, isopropyl, butyl, isobutyl, t-butyl, pentyl, hexyl, ethenyl, propenyl, buenyl, cyclopropyl, cyclobutyl, cyclopentyl, cyclohexyl, etc. Whenever a substituted is described as being "optionally substituted", that substituent may be substituted with one of the above substituents.

"Sulfanyl" refers to the —SR group, where R may be alkyl, cyclic hydrocarbyl, heterocyclyl, aryl, heteroaryl, and the like, as defined above. Examples of sulfanyl include, but are not limited to, —$SCH_3$ and —$SCH_2CH_3$.

"Acyl" refers to the —C(=O)R group, where R is a group such as an alkyl as defined above (herein referred as alkylacyl), cyclic hydrocarbyl (herein referred as cyclic hydrocarbyl acyl), heterocyclyl (herein referred as heterocyclyl acyl), aryl (herein referred as aryl acyl), heteroaryl (herein referred as heteroaryl acyl) and the like. Examples of acyl include, but are not limited to, —C(=O)$CH_3$ (acetyl), —C(=O)$CH_2CH_3$ (propionyl), —C(=O)C($CH_3$)$_3$ (butyryl) and —C(=O)Ph (benzoyl or benzophenone).

"Amide" refers to the —$NR^1$C(=O)$R^2$ group, where $R^1$ and $R^2$ may be independently hydrogen, or a group such as alkyl, cyclic hydrocarbyl, heterocyclyl, aryl, heteroaryl, and the like, as defined above. Examples of amide include, but are not limited to, —NHC(=O)H (formamido), —NHC(=O)$CH_3$ (acetamido) and —NHC(=O)NHPh (benzamido).

"Sulfinyl" refers to the —S(=O)R group, where R may be alkyl, cyclic hydrocarbyl, heterocyclyl, aryl, heteroaryl, and the like, as defined above. Examples of sulfinyl include, but are not limited to —S(=O)$CH_3$ and —S(=O)$CH_2CH_3$.

"Sulfonyl" refers to the —S(=O)$_2$R group, where R may be alkyl, cyclic hydrocarbyl, heterocyclyl, aryl, heteroaryl, and the like, as defined above. Examples of sulfonyl include, but are not limited to, —S(=O)$_2$$CH_3$ (mesyl), —S(=O)$_2$$CF_3$, —S(=O)$_2$$CH_2CH_3$ and 4-methylphenylsulfonyl(tosyl).

"Prodrug" is meant to indicate to a compound which can be converted under physiological conditions or by solvolysis to a biologically active compound of the present application. Therefore, the term "prodrug" refers to a metabolic precursor of a compound of the present application that is pharmaceutically acceptable. A prodrug may be inactive when administrated to a subject in need thereof, but is converted in vivo to an active compound of the present application. Prodrugs are typically rapidly transformed in vivo to yield the parent compound of the present application, for example, by hydrolysis in blood. The prodrug compound often provides advantages of solubility, tissue compatibility or controlled-release in organism of mammals (see, Bundgard, H., Design of Prodrugs (1985), pp. 7-9, 21-24 (Elsevier, Amsterdam)).

A discussion of prodrugs is provided in Higuchi, T., et al, "Pro-drugs as Novel Delivery Systems" A.C.S. Symposium Series, Vol. 14, and Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the present application in vivo when such a prodrug is administrated to a mammal subject. Prodrugs of a compound of the present application can be prepared by modifying a functional group present in the compound of the present application in such a way that the modifications are cleaved either in routine manipulation or in vivo, to the parent compound of the present application. Prodrugs include compounds of the present application, wherein hydroxy, amino or mercapto group is bonded to any group that, when the prodrug of a compound of the present application is administrated to a mammal subject, cleaves to form free hydroxy, free amino or free mercapto group, respectively. Examples of a prodrug include, but are not limited to, acetate, formate and benzoate derivatives of alcohol or amine functional groups in the compound of the present application and the like.

"Metabolite" is intended to refer to that the active compound of the present application can be converted into an organic compound under physiological condition or in vivo. Moreover, its chemical structure may be similar to or quite different from that of the active compound of the present application, and generally, have certain bioactivity. The formation of the "metabolite" may be in either a human circulatory system such as blood, or other tissues or cells. Sometimes, the "metabolite" provides advantages such as solubility, histocompatibility or controlled-release in an organism of a mammal.

"Optional" or "optionally" means that the subsequently described event of circumstances may or may not occur, and that the description includes instances where said events or circumstances occur and instance in which it does not. For example, "optionally substituted aryl" means that the aryl group may or may not be substituted and the description includes both substituted aryl groups and aryl groups having no substitution.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effects on preparing a pharmaceutical composition.

"Pharmaceutically acceptable salts" include both "pharmaceutically acceptable acid addition salts" and "pharmaceutically acceptable base addition salts".

"Pharmaceutically acceptable acid addition salt" refers to those salts which retain the biological effectiveness and properties of the free bases, which are not biologically or otherwise undesirable, and which are formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic or an organic base to the free acid. Salts derived from inorganic bases include, but are not limited to, sodium, potassium, lithium, ammonium, calcium, magnesium, iron, zinc, copper, manganese, aluminum slats, and the like. Preferred inorganic salts are the ammonium, sodium, potassium, calcium, and magnesium salts. Salts derived from organic bases include, but are not limited to, slats of primary, secondary and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminethanol, dicyclohexylamine, lysine, arginine, histidine, caffeine, procaine, hydrabamine, choline, betaine, benethamine, benzathine, ethylenediamine, glucosamine, methylglucosamine, theobromine, triethanolamine, trometamol, purine, piperazine, piperidine, N-ethyl piperidine, polyamine resin and the like. Particularly preferred organic bases are isopropylamine, diethylamine, ethanolamine, trimethylamine, dicyclohexylamine, choline and caffeine.

A "pharmaceutical composition" refers to a formulation of a compound of the present application and a medium generally accepted in the art for the delivery of the biologically active compound to a subject. Such a medium includes all pharmaceutically acceptable carriers.

A pharmaceutical composition comprising a compound of general formula (I) can be prepared according to formulation and be used as following dosage form: tablets, capsules or elixir for oral administration; suppository for rectal administration; sterile solution, suspension for injection administration; patch for transdermal administration and subcutaneous sediments, and the like. The injection may be prepared as the following forms: solution or suspension, a solid dosage form suitably being prepared as solution or suspension prior to injection, or emulsion. Suitable excipient may be for example, water, saline, glucose, mannitol, lactose, lecithin, albumin, sodium glutamate, cysteine hydrochloride, and the like. Additionally, if necessary, the pharmaceutical composition for injection may contain few amounts of nontoxic auxiliaries such as wetting agent, pH buffer and the like. If necessary, absorption reinforcing agent (such as liposome) may be used.

Preparation for parenteral administration may contain an aqueous solution of the active compound in the form of aqueous solution. Additionally, the suspension of the active compound can be prepared as suitable oily injection suspension. Suitable lipotropic solvent or carrier includes fatty oils such as sesame oil, or other organic oil such as soybean oil, pomelo oil, apricot kernel oil, or aliphatic ester such as ethyl oleate or triglyceride, or liposome. Aqueous injection suspension may include a substance for enhancing the viscosity of the suspension, such as sodium carboxymethylcellulose, sorbitol or glucan. Optionally, the suspension may include suitable stabilizer or reagent for improving the solubility of the compound, so as to prepare a solution having high concentration.

A pharmaceutical preparation for oral administration can be obtained as following process: contacting the active compound with solid excipient, and the resultant mixture is optionally grounded, and the granular mixture is processed, if necessary, suitable adjuvant is added so as to obtain tablets or sugarcoat agent core. Suitable excipient is specifically filler such as sugar, including lactose, saccharose, mannitol or sorbitol; cellulose preparation such as corn starch, wheat starch, rice starch, potato starch, gelatin, tragacanth, methylcellulose, hydroxypropyl methyl cellulose, sodium carboxymethyl cellulose, and/or polyvinylpyrrolidone (PVP). If necessary, the disintegrant may be added, such as crosslinked polyvinylpyrrolidone, agar or alginic acid or alginate such as sodium alginate. The sugarcoat agent core can be suitably coated. For this purpose, concentrated sugar solution can be used, and this solution can optionally comprise acacia, talc, polyvinylpyrrolidone, polycarboxyvinyl gels, polyethylene glycol and/or titanium dioxide, lacquer solution and suitable organic solvent or mixture of solvents. For recognizing or expressing the features of different combinations of the dose of the active compound, a dye or pigment can be added into tablets or sugarcoat agent coating. These preparations can be produced according to well-known methods in the art.

The present application is also directed to various pharmaceutical compositions for delivery such as intraocular delivery, nasal delivery and in-ear delivery, as well-known in the art. Pharmaceutical formulation includes aqueous ophthalmic solution of the active compound, which can be present in the form of aqueous solution such as eye drops, or gellengums or hydrogels; ophthalmic ointment; ophthalmic suspension, such as particle, small aggregated particle having medicine suspended in liquid carrier medium, liposoluble preparation, and microbeads; and ophthalmic implant. For stability and comfortability, these suitable pharmaceutical preparations are more often and preferably prepared as sterile, isotomic and buffered preparation. Pharmaceutical composition also includes drops and sprays, and usually imitate nose secretion in many ways so as to ensure the maintenance of the normal cilium effect. As known by a person having ordinary skill in the art, suitable preparation is most often and preferably isotonic and slightly buffered at pH of 5.5 to 6.5, and most often and preferably contains an antibiotic preservative and suitable a pharmaceutical stabilizer. Pharmaceutical preparation for transportation in ear includes suspension and ointment which is locally applied in the ear. Common solvents for these ear preparations include glycerol and water.

While used as a compound for inhibition of PARP, a compound of general formula (I) or a pharmaceutical composition comprising the compound of general formula (I) can be administered through oral routine or non-oral routine. While orally administered, it can be administered as capsule, tablet, granule, spray, syrup or other dosage form. While non-orally administered, it can be administered as aqueous suspension, oily preparation, etc, or drop, suppository, unction, ointment, etc. While administered by injection, it can be administered by means of subcutaneous routine, intraperitoneal routine, intravenous routine, intramuscular routine.

"Therapeutically effective amount" refers to that amount of a compound of the present application which, when administered to a subject such as a mammal, preferably a human, is sufficient to effect treatment, as defined below, of a disease or condition mediated by PARP in the subject such as a mammal, preferably a human. The amount of a compound of the present application which constitutes a "therapeutically effective amount" will vary depending on the selected compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a subject such as a mammal, preferably a human, having the disease or disorder of interest, and includes:

(i) preventing the disease or condition from occurring in a subject such as a mammal, in particular, when the subject such as a mammal is predisposed to the condition but has not yet been diagnosed as having it;

(ii) inhibiting the disease or condition, i.e. arresting its development; or (iii) relieving the disease or condition, i.e. causing regression of the disease or condition.

Throughout the treatment course, the administration in vivo can be carried out by means of single administration, continuous administration or interval administration (such as the administration is carried out by divided dose and appropriate intervals). The method for determining the most effective administration manner and dose would have been well-known for a person having ordinary skill in the art, and varies depending on the preparation to be used in the treatment, the object of the treatment, the targeted cell of the treatment and the subject to be treated. It can be carried out by single or multiple administrations, and the level of dose and mode can be selected by attending doctor.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, the term "contact" refers to that two or more substances get close each other to interact.

"A stereoisomer" refers to a compound consisting of identical atoms bonded by identical chemical bonds, but having different three-dimensional structures which are uninterchangeably. The present application covers various stereoisomers and mixtures thereof.

The compounds of the present application, or their pharmaceutically acceptable salts may contain one or more asymmetric centers and may thus give rise to enantiomers, diastereoisomers, and other stereoismeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers can be prepared using chiral synthons or chiral reagents, or resolved using conventional techniques such as HPLC using a chiral column. When the compounds described herein contain olefinic double bonds or other centers of geometric asymmetry, and unless specified otherwise, it is intended that the compounds include E and Z geometric isomers. Likewise, all tautomeric forms are also intended to be included.

Embodiments

In one aspect, the present application is directed to a compound of general formula (I), a single stereoisomer thereof, or a mixture of stereoisomers, a pharmaceutically acceptable salt thereof, a prodrug thereof, or a metabolite thereof:

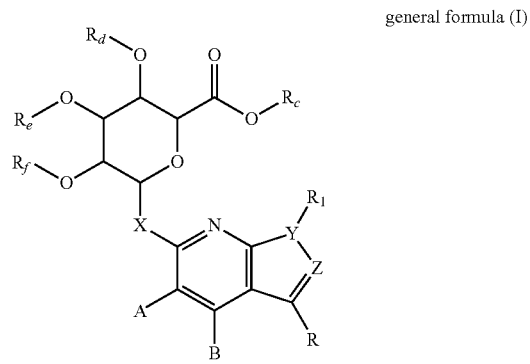

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of oxygen and sulphur; and

Y and Z are independently selected from the group consisting of nitrogen, oxygen, sulphur and optionally substituted methylene.

In some embodiments, optionally substituted alkyl is optionally substituted $C_1$-$C_{12}$ alkyl.

In some embodiments, optionally substituted alkyl is optionally substituted $C_1$-$C_8$ alkyl.

In some embodiments, optionally substituted alkyl is optionally substituted $C_1$-$C_6$ alkyl.

In some embodiments, optionally substituted alkoxy is optionally substituted $C_1$-$C_{12}$ alkoxy.

In some embodiments, optionally substituted alkoxy is optionally substituted $C_1$-$C_8$ alkoxy.

In some embodiments, optionally substituted alkoxy is optionally substituted $C_1$-$C_6$ alkoxy.

In some embodiments, optionally substituted haloalkyl is optionally substituted $C_1$-$C_{12}$ haloalkyl.

In some embodiments, optionally substituted haloalkyl is optionally substituted $C_1$-$C_8$ haloalkyl.

In some embodiments, optionally substituted haloalkyl is optionally substituted $C_1$-$C_6$ haloalkyl.

In some embodiments, optionally substituted haloalkoxy is optionally substituted $C_1$-$C_{12}$ haloalkoxy.

In some embodiments, optionally substituted haloalkoxy is optionally substituted $C_1$-$C_8$ haloalkoxy.

In some embodiments, optionally substituted haloalkoxy is optionally substituted $C_1$-$C_6$ haloalkoxy.

In some embodiments, optionally substituted cyclohydrocarbyl is optionally substituted $C_3$-$C_{15}$ cyclohydrocarbyl.

In some embodiments, optionally substituted cyclohydrocarbyl is optionally substituted $C_3$-$C_{12}$ cyclohydrocarbyl.

In some embodiments, optionally substituted heterocyclyl is optionally substituted $C_2$-$C_{13}$ heterocyclyl.

In some embodiments, optionally substituted heterocyclyl is optionally substituted $C_3$-$C_{10}$ heterocyclyl.

In some embodiments, optionally substituted aryl is optionally substituted $C_6$-$C_{19}$ aryl.

In some embodiments, optionally substituted aryl is optionally substituted $C_6$-$C_{10}$ aryl.

In some embodiments, optionally substituted arylalkyl is optionally substituted $C_7$-$C_{31}$ arylalkyl.

In some embodiments, optionally substituted arylalkyl is optionally substituted $C_7$-$C_{27}$ arylalkyl.

In some embodiments, optionally substituted arylalkyl is optionally substituted $C_7$-$C_{16}$ arylalkyl.

In some embodiments, optionally substituted heteroaryl is optionally substituted $C_4$-$C_{13}$ heteroaryl.

In some embodiments, optionally substituted heteroaryl is optionally substituted $C_4$-$C_9$ heteroaryl.

In some embodiments, A and B together with carbons to which A and B attach represent optionally substituted $C_6$-$C_{19}$ aryl, optionally substituted $C_4$-$C_{13}$ heteroaryl, optionally substituted $C_3$-$C_{15}$ cyclohydrocarbyl, or optionally substituted $C_2$-$C_{13}$ heterocyclohydrocarbyl.

In some embodiments, A and B together with carbons to which A and B attach represent optionally substituted $C_6$-$C_{10}$ aryl, optionally substituted $C_4$-$C_9$ heteroaryl, optionally substituted $C_3$-$C_{12}$ cyclohydrocarbyl, or optionally substituted $C_3$-$C_{10}$ heterocyclohydrocarbyl.

In some embodiments, A and B together with carbons to which A and B attach represent optionally substituted aryl, or optionally substituted cyclic hydrocarbyl.

In some embodiments, A and B together with carbons to which A and B attach represent optionally substituted $C_6$-$C_{19}$ aryl, or optionally substituted $C_3$-$C_{15}$ cyclohydrocarbyl.

In some embodiments, A and B together with carbons to which A and B attach represent optionally substituted $C_6$-$C_{10}$ aryl, or optionally substituted $C_3$-$C_{10}$ cyclohydrocarbyl.

In some embodiments, A and B together with carbons to which A and B attach represent optionally substituted phenyl, optionally substituted cyclopentyl, or optionally substituted cyclohexyl.

In some embodiments, X is oxygen.

In some embodiments, Y and Z are each nitrogen.

In some embodiments, $R_1$ is selected from the group consisting of hydrogen, optionally substituted alkyl and optionally substituted haloalkyl.

In some embodiments, $R_1$ is selected from the group consisting of hydrogen, optionally substituted $C_1$-$C_{12}$ alkyl and optionally substituted $C_1$-$C_{12}$ haloalkyl.

In some embodiments, $R_1$ is selected from the group consisting of hydrogen, optionally substituted $C_1$-$C_8$ alkyl and optionally substituted $C_1$-$C_8$ haloalkyl.

In some embodiments, $R_1$ is selected from the group consisting of hydrogen, optionally substituted $C_1$-$C_6$ alkyl and optionally substituted $C_1$-$C_6$ haloalkyl.

In some embodiments, $R_1$ is methyl.

In some embodiments, R is selected from the group consisting of hydrogen, optionally substituted alkyl, optionally substituted haloalkyl, optionally substituted cyclohydrocarbyl and optionally substituted heterocyclyl.

In some embodiments, R is selected from the group consisting of alkyl, phenyl, alkylpyrrolidinyl, haloalkylpyrrolidinyl, cyclohydrocarbylpyrrolidinyl and alkylpiperidyl.

In some embodiments, R is selected from the group consisting of $C_1$-$C_{12}$ alkyl, phenyl, $C_1$-$C_{12}$ alkylpyrrolidinyl, $C_1$-$C_{12}$ haloalkylpyrrolidinyl, $C_3$-$C_{15}$ cyclohydrocarbylpyrrolidinyl and $C_1$-$C_{12}$ alkylpiperidyl.

In some embodiments, R is selected from the group consisting of $C_1$-$C_8$ alkyl, phenyl, $C_1$-$C_8$ alkylpyrrolidinyl, $C_1$-$C_8$ haloalkylpyrrolidinyl, $C_3$-$C_{12}$ cyclohydrocarbylpyrrolidinyl and $C_1$-$C_8$ alkylpiperidyl.

In some embodiments, R is selected from the group consisting of $C_1$-$C_6$ alkyl, phenyl, $C_1$-$C_8$ alkylpyrrolidinyl, $C_1$-$C_6$ haloalkylpyrrolidinyl, $C_3$-$C_{12}$ cycloalkylpyrrolidinyl and $C_1$-$C_6$ alkylpiperidyl.

In some embodiments, R is selected from the group consisting of methyl, isopropyl, phenyl, ethylpyrrolidinyl, propylpyrrolidinyl, trifluoropropylpyrrolidinyl, cyclopentylpyrrolidinyl, ethylpiperidyl and propylpiperidyl.

In some embodiments, $R_c$, $R_d$, $R_e$ and $R_f$ are independently selected from the group consisting of hydrogen and optionally substituted alkyl.

In some embodiments, $R_c$, $R_d$, $R_e$ and $R_f$ are independently selected from the group consisting of hydrogen and optionally substituted $C_1$-$C_{12}$ alkyl.

In some embodiments, $R_c$, $R_d$, $R_e$ and $R_f$ are independently selected from the group consisting of hydrogen and optionally substituted $C_1$-$C_8$ alkyl.

In some embodiments, $R_c$, $R_d$, $R_e$ and $R_f$ are independently selected from the group consisting of hydrogen and optionally substituted $C_1$-$C_6$ alkyl.

In some embodiments, $R_c$, $R_d$, $R_e$ and $R_f$ are each hydrogen.

In some embodiments, the compound of general formula (I) is selected from the group consisting of:

(2S,3S,4S,5R,6S)-6-(1,3-dimethyl-6,7,8,9-tetrahydro-3H-pyrazolo[3,4-c]isoquinoline-5-oxy)-3,4,5-trihydroxytetrahydro-2H-pyran-2-formic acid;

(2S,3S,4S,5R,6S)-3,4,5-trihydroxy-6-(1-isopropyl-3-methyl-6,7,8,9-tetrahydro-3H-pyrazolo[3,4-c]isoquinoline-5-oxy)-tetrahydro-2H-pyran-2-formic acid;

(2S,3S,4S,5R,6S)-3,4,5-trihydroxy-6-(1-phenyl-3-methyl-6,7,8,9-tetrahydro-3H-pyrazolo[3,4-c]isoquinoline-5-oxy)-tetrahydro-2H-pyran-2-formic acid;

(2S,3S,4S,5R,6S)-3,4,5-trihydroxy-6-(3-methyl-1-((R)-1-propylpyrrolidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-((S)-1-propylpyrrolidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-ethylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-(3,3-trifluoropropyl)pyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-((R)-1-propylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-((S)-1-propylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(1-(1-ethylpiperidin-2-yl)-3-methyl-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpiperidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpiperidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpiperidin-4-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpyrrolidin-3-yl)-3,6,7,8-tetrahydrocyclopentano[d]pyrazolo[3,4-b]pyridine-5-oxy)tetrahydro-2H-pyran-2-formic acid;

(2S,3S,4S,5R,6S)-3,4,5-trihydroxy-6-(3-methyl-1-(1-propylpyrrolidin-3-yl)-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-cyclopentylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(R)-1-isopropylpyrrolidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-triacetyl-6-(1,3-dimethyl-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(1-isopropyl-3-methyl-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(3-methyl-1-phenyl-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(3-methyl-1-((R)-1-propylpyrrolidin-2-yl)-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-trihydroxy-6-(3-methyl-1-((S)-1-propylpyrrolidin-2-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpyrrolidin-3-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-ethylpyrrolidin-3-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-(3,3-trifluoropropyl)pyrrolidin-3-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-triacetyl-6-(3-methyl-1-((R)-1-propylpyrrolidin-3-yl)-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(3-methyl-1-((S)-1-propylpyrrolidin-3-yl)-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(1-(1-ethylpiperidin-2-yl)-3-methyl-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpiperidin-2-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpiperidin-3-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpiperidin-4-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpyrrolidin-3-yl)-3,6,7,8-tetrahydrocyclopentano[d]pyrazolo[3,4-b]pyridine-5-oxy)tetrahydro-2H-pyran-2-methylformate;

(2S,3S,4S,5R,6S)-3,4,5-trihydroxy-6-(3-methyl-1-(1-propylpyrrolidin-3-yl)-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-cyclopentylpyrrolidin-3-yl)-6,7,8,9-tetrahydro-3H-pyrazolo[3,4-c] isoquinoline-5-oxy)tetrahydro-2H-pyran-2-methylformate; and (2S,3S,4S,5R, 6S)-3,4,5-trihydroxy-6-(3-methyl-1-(R)-1-isopropylpyrrolidin-2-yl)-6,7,8,9-tetrahydro-3H-pyrazolo[3,4-c]isoquinoline-5-oxy)tetrahydro-2H-pyran-2-methylformate.

In another aspect, the present application is directed to a process for preparing a compound of general formula (I), comprising reacting a compound of general formula (XIV) and a compound of general formula (VI) to obtain the compound of general formula (I),

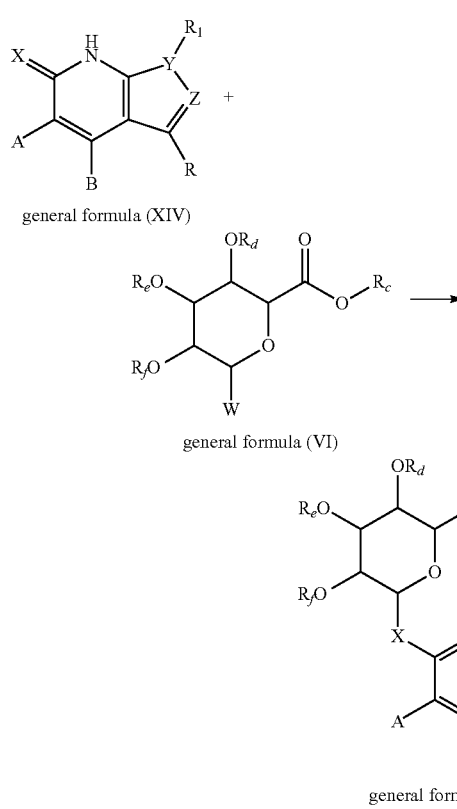

general formula (XIV)

general formula (VI)

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

W is halogen;

X is selected from the group consisting of oxygen and sulphur; and

Y and Z are independently selected from the group consisting of nitrogen, oxygen, sulphur and optionally substituted methylene.

In some embodiments, a compound of general formula (XIV) reacts with a compound of general formula (VI) in the presence of a base to obtain a compound of general formula (I).

In some embodiments, a compound of general formula (XIV) firstly reacts with sodium hydride to obtain a resultant product, the product is treated with silver nitrate, and then reacts with a compound of general formula (VI) to obtain a compound of general formula (I).

In still another aspect, the present application is directed to a pharmaceutical composition, comprising a pharmaceutically acceptable carrier and a therapeutically effective amount of a compound of general formula (I), a single stereoisomer thereof, or a mixture of stereoisomers, a pharmaceutically acceptable salt thereof, a prodrug thereof, or a metabolite thereof:

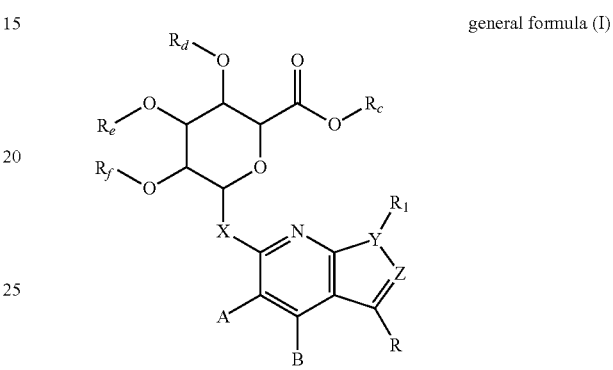

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of oxygen and sulphur; and

Y and Z are independently selected from the group consisting of nitrogen, oxygen, sulphur and optionally substituted methylene.

In some embodiments, the pharmaceutical composition further comprises at least another active ingredient.

Exemplary active ingredients that can be used in the present application include, but are not limited to, nitrogen mustard, aziridine, methylmelamine, alkyl sulphonate, nitrosourea, triazene, folacin, pyrimidine analogue, purine analogue, vinca alkaloid, epipodophyllotoxin, antibiotic, topoisomerase inhibitor, anticancer vaccine, acivicin, aclarubicin hydrochloride acodazole, acronine, adozelesin, aldesleukin, ambomycin, ametantrone acetate, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin, droloxifene hydrochloride, epirubicin hydrochloride, esorubicin hydrochloride, estramustine, etanidazole, etoposide, floxuridine, fluorouracil, fluorocitabine, gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, angiogenesis inhibitor, camptothecin, hexadecadrol, aspirin, acetaminophen, indometacin, ibuprofen, ketoprofen, meloxicam, corticosteroid and adrenal corticosteroid.

In yet another aspect, the present application is directed to a process for inhibiting activities of poly(ADP-ribose)polymerase (PARP), comprising contacting a therapeutically effective amount of a compound of general formula (I), a single stereoisomer thereof, or a mixture of stereoisomers, a pharmaceutically acceptable salt thereof, a prodrug thereof, or a metabolite thereof, with PARP,

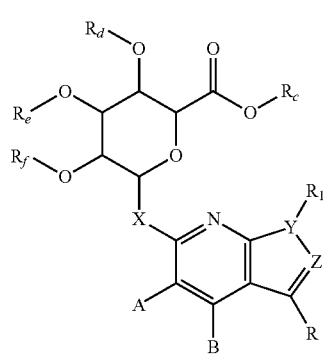

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of oxygen and sulphur; and

Y and Z are independently selected from the group consisting of nitrogen, oxygen, sulphur and optionally substituted methylene.

In some embodiments, the method for inhibiting activities of poly(ADP-ribose)polymerase (PARP) is carried out in vitro.

In some embodiments, the contacting may be carried out in a vessel, such as a test tube, petri culture dish, and the like.

In some embodiments, the contacting may be carried out in the presence of other substances.

In some embodiments, the contacting may be carried out in the presence of a cell.

In some embodiments, one or more contacted substances may be inside cells. The cells may be viable or dead. The cell may be complete or incomplete.

In still another aspect, the present application is directed to a process for treating a disease or condition mediated poly (ADP-ribose)polymerase (PARP), comprising contacting a therapeutically effective amount of a compound of general formula (I), a single stereoisomer thereof, or a mixture of stereoisomers, a pharmaceutically acceptable salt thereof, a prodrug thereof, or a metabolite thereof,

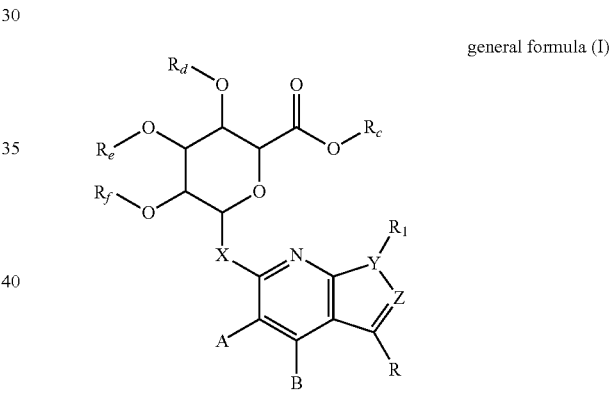

general formula (I)

wherein:

A and B are independently selected from the group consisting of hydrogen, optionally substituted alkyl, optionally substituted alkoxy, optionally substituted haloalkyl, optionally substituted haloalkoxy, optionally substituted cyclohydrocarbyl, optionally substituted heterocyclohydrocarbyl, optionally substituted aryl, optionally substituted arylalkyl, optionally substituted heteroaryl, halogen, hydroxy, nitro, amino, optionally substituted amido, mercapto, optionally substituted sulfanyl, optionally substituted sulfinyl and optionally substituted sulfonyl; or A and B together with carbons to which A and B attach represent optionally substituted aryl, optionally substituted heteroaryl, optionally substituted cyclohydrocarbyl, or optionally substituted heterocyclohydrocarbyl;

$R_c$, $R_d$, $R_e$ and $R_f$ are independently selected from the group consisting of hydrogen, optionally substituted alkyl and optionally substituted acyl;

$R_1$ and R are independently selected from the group consisting of hydrogen, optionally substituted alkyl, optionally substituted haloalkyl, optionally substituted cyclohydrocarbyl, optionally substituted heterocyclyl, optionally substituted aryl, optionally substituted arylalkyl and optionally substituted heteroaryl;

X is selected from the group consisting of nitrogen, oxygen and sulphur; and

Y and Z are independently selected from the group consisting of nitrogen, oxygen, sulphur and optionally substituted methylene.

In some embodiments, exemplary diseases or conditions mediated poly(ADP-ribose)polymerase (PARP) include, but are not limited to, inflammatory disease or condition, infectious disease or condition, immune disease or condition, cancer disease or condition, and degenerative disease or condition.

In some embodiments, examples of diseases or conditions mediated poly(ADP-ribose)polymerase (PARP) include, but are not limited to, head carcinoma, thyroid carcinoma, neck cancer, eye cancer, skin cancer, oral cancer, throat cancer, esophagus cancer, breast cancer, bone cancer, leukemia, myeloma, lung cancer, colon cancer, sigmoid colon, carcinoma, rectal cancer, gastric cancer, prostate cancer, breast cancer, ovarian cancer, kidney cancer, liver cancer, pancreatic cancer, brain cancer, intestinal cancer, heart cancer, adrenal carcinoma, subcutaneous tissue cancer, lymph node cancer, malignant melanoma, malignant glioma, HIV, hepatitis, adult respiratory distress syndrome, bone absorption disease, chronic obstructive pulmonary disease, chronic pneumonia, dermatitis, inflammatory skin disease, atopic dermatitis, cystic fibrosis, septic shock, pyaemia, endotoxin shock, blood dynamic shock, septic disease syndrome, ischemia reperfusion injury, meningitis, psoriasis, fibrosis disease, cachexia, graft rejection of graft versus host disease, autoimmunity disease, rheumatoidspondylitis, arthritis symptom (such as rheumatoid arthritis or osteoarthritis), osteoporosis, Crohn's disease, ulcerative colitis, enteritis, multiple sclerosis, systemic lupus erythematosus, erythema nodosum leprosum of leprosy (ENL), radiation damage, asthma, oxygen enriched lung injury, microorganism infection and microorganism infection syndrome.

In some embodiments, to a subject in need of treating a disease or condition mediated by poly(ADP-ribose)polymerase (PARP) is administered a unit dose of 0.1 mg to 1,000 mg of a compound of general formula (I), a single stereoisomer thereof, or a mixture of stereoisomers, a pharmaceutically acceptable salt thereof, a prodrug thereof, or a metabolite thereof.

In some embodiments, to a subject in need of treating a disease or condition mediated by poly(ADP-ribose)polymerase (PARP) is administered a unit dose of 1 mg to 1,000 mg of a compound of general formula (I), a single stereoisomer thereof, or a mixture of stereoisomers, a pharmaceutically acceptable salt thereof, a prodrug thereof, or a metabolite thereof.

In some embodiments, the method for treating a disease or condition mediated by poly(ADP-ribose)polymerase (PARP), comprising administering to a subject in need thereof a therapeutically effective amount of a compound of general formula (I), a single stereoisomer thereof, or a mixture of stereoisomers, a pharmaceutically acceptable salt thereof, a prodrug thereof, or a metabolite thereof, and at least another active ingredient.

Exemplary active ingredients that can be used in the present application include, but are not limited to, nitrogen mustard, aziridine, methylmelamine, alkyl sulphonate, nitrosourea, triazene, folacin, pyrimidine analogue, purine analogue, vinca alkaloid, epipodophyllotoxin, antibiotic, topoisomerase inhibitor, anticancer vaccine, acivicin, aclarubicin, hydrochloride acodazole, acronine, adozelesin, aldesleukin, ambomycin, ametantrone acetate, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin, droloxifene hydrochloride, epirubicin hydrochloride, esorubicin hydrochloride, estramustine, etanidazole, etoposide, floxuridine, fluorouracil, fluorocitabine, gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, angiogenesis inhibitor, camptothecin, hexadecadrol, aspirin, acetaminophen, indometacin, ibuprofen, ketoprofen, meloxicam, corticosteroid or adrenal corticosteroid.

In some embodiments, a therapeutically effective amount of a compound of general formula (I), a single stereoisomer thereof, or a mixture of stereoisomers, a pharmaceutically acceptable salt thereof, a prodrug thereof, or a metabolite thereof, and at least another active ingredient are simultaneously, synergistically, separately or sequentially administered to a subject in need of a method for treating a disease or condition mediated by poly(ADP-ribose)polymerase (PARP).

Preparation of Compounds of Present Application

It should be understood, in the following illustration, only when the combination of the substituents and/or the variation of the general formula can obtain stable compounds, such combination of the substitutes and/or variation of the general formula will be permitted.

An experienced person having ordinary skills in the art can understand that, in the following process; the functional groups of intermediate compounds may be protected with appropriate protecting groups. Such functional groups include hydroxy, amino, mercapto and carboxylic acid. Suitable hydroxy protecting groups include trialkylsilyl or diarylalkylsilyl (such as t-butyldimethylsilyl, t-butyldiphenylsilyl or trimethylsilyl), tetrahydropyranyl, benzyl, and the like. Suitable amino, imidazolyl and guanidyl protecting groups include t-butoxycarbonyl, benzyloxycarbonyl, and the like. Suitable mercapto protecting groups include —C(O)—R" (wherein R" is alkyl, aryl or arylalkyl), p-methoxybenzyl, trityl, and the like. Suitable carboxylic acid protecting groups include alkyl, aryl or arylalkyl esters.

The protecting groups can be introduced or removed according to standard technique well-known by an experienced person having ordinary skills in the art and described herein.

The process for preparing the compounds of the present application is illustrated in the following reaction schemes. It should be understood, a person having ordinary skill in the art can prepare these compounds by a similar process or a process known by a person having ordinary skill in the art.

Generally, a compound of general formula (I) of the present application can be prepared according to the general process as described in reaction scheme 1, wherein X is oxygen, Y and Z are each N, A and B together with carbons to which A and B attach represent phenyl.

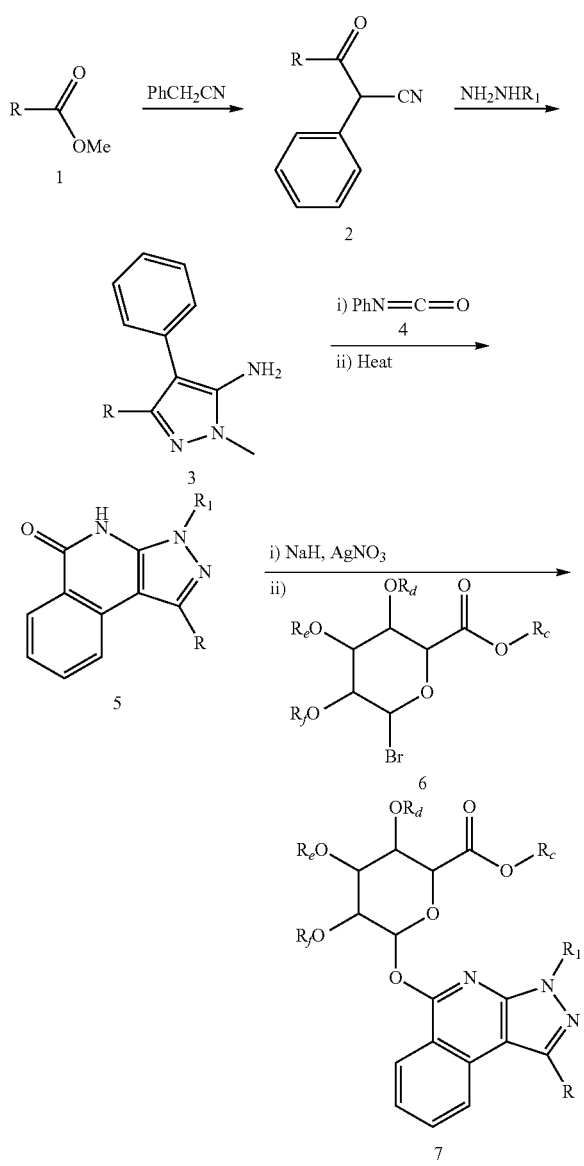

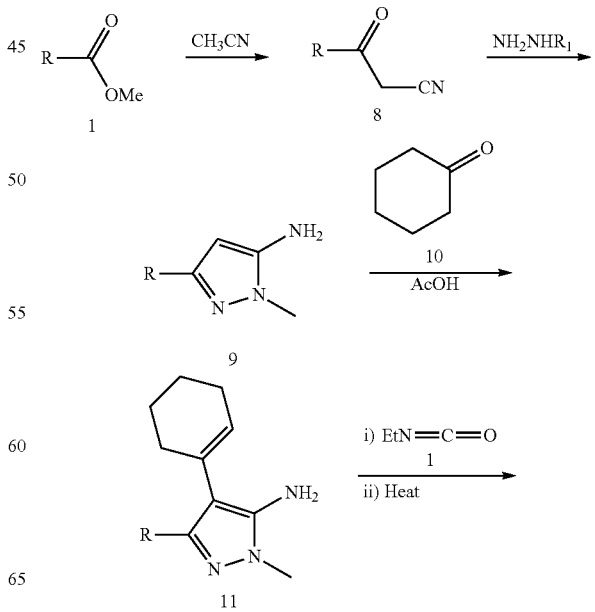

tive ions are treated with ester of compound 1 to produce compound 2. The reaction is also suitable for preparing derivatives of a compound of the present application, in which phenyl ring comprises other substituents, by substituting the phenylacetonitrile beforehand.

(2) Compound 2 comprising one β-carbonyl substituted acetonitrile structure and methylhydrazine or derivatives thereof are heated to form 5-aminopyrozole derivatives 3. In this step of the reaction, the heating can be carried out with solvent such as alcohol, or the heating is carried out directed with methylhydrazine derivatives, wherein $R_1$ is selected from the group consisting of hydrogen, optionally substituted $C_1$-$C_{12}$ alkyl, optionally substituted $C_1$-$C_{12}$ haloalkyl, optionally substituted $C_3$-$C_{15}$ cyclic hydrocarbyl, optionally substituted $C_2$-$C_{13}$ heterocyclyl, optionally substituted $C_6$-$C_{19}$ aryl, optionally substituted $C_7$-$C_{31}$ arylalkyl and optionally substituted $C_4$-$C_{13}$ heteroaryl. The active functional groups in the starting material include, but are not limited to, any one to four selected from the group consisting of nitrogen, oxygen and sulphur, $C_3$-$C_{12}$ heterocyclyl, hydroxy, amino, and the like. The active functional groups shall be protected with inert protecting groups.

(3) Compound 3 reacts with phenyl isocyanate to form an adduct having relatively lower solubility at room temperature. The intermediate is heated to carry out cyclization to give compound 5.

(4) The compound 5 is dehydrogenated with sodium hydride and then treated with silver nitrate to obtain a silver slat intermediate. The intermediate reacts with known compound 6 to give compound 7 of the present application. Alternatively, compound 5 reacts with known compound 6 in the presence of silver oxide to give compound 7 of the present application.

Finally, the protecting groups can be deprotected by a process known in the art to give a compound of the present application.

Generally, a compound of general formula (I) of the present application can be prepared according to a general process as described in reaction scheme 2, wherein X is oxygen, both Y and Z are N, A and B together with carbons to which A and B attach represent cyclohexyl.

The starting materials in the above reaction scheme are commercially available, or can be prepared according to a process known by a person having ordinary skill in the art or a process disclosed herein. Generally, the compounds of the present application can be prepared according to the above reaction scheme as follows:

(1) The preparation of β-carbonyl substituted acetonitrile 2. R in the starting material compound 1 is selected from the group consisting of hydrogen, optionally substituted $C_1$-$C_{12}$ alkyl, optionally substituted $C_1$-$C_{12}$ haloalkyl, optionally substituted $C_3$-$C_{15}$ cyclic hydrocarbyl, optionally substituted $C_2$-$C_{13}$ heterocyclyl, optionally substituted $C_6$-$C_{19}$ aryl, optionally substituted $C_7$-$C_{31}$ arylalkyl and optionally substituted $C_4$-$C_{13}$ heteroaryl. The active functional groups in the starting material include, but are not limited to, any one to four selected from the group consisting of nitrogen, oxygen and sulphur, $C_3$-$C_{12}$ heterocyclyl, hydroxy, amino, and the like. The active functional groups shall be protected with inert protecting groups. In the reaction, phenylacetonitrile is firstly dehydrogenated with strong base including, but not limited to, n-butyl lithium, to form negative ions. The resultant nega- -continued

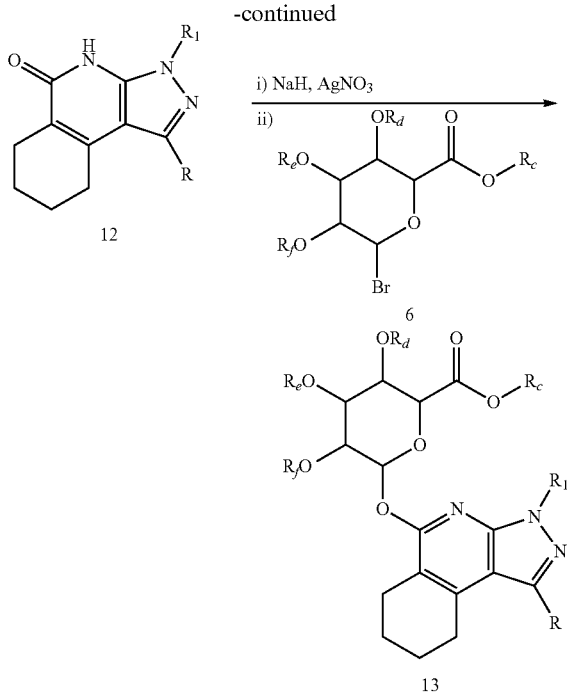

The starting materials in the above reaction scheme are commercially available, or can be prepared according to a process known by a person having ordinary skill in the art or a process disclosed herein. Generally, the compounds of the present application can be prepared according to the above reaction scheme as follows:

(1) The preparation of β-carbonyl substituted acetonitrile 8. R in the starting material compound 1 is selected from the group consisting of hydrogen, optionally substituted $C_1$-$C_{12}$ alkyl, optionally substituted $C_1$-$C_{12}$ haloalkyl, optionally substituted $C_3$-$C_{15}$ cyclic hydrocarbyl, optionally substituted $C_2$-$C_{13}$ heterocyclyl, optionally substituted $C_6$-$C_{19}$ aryl, optionally substituted $C_7$-$C_{31}$ arylalkyl and optionally substituted $C_4$-$C_{13}$ heteroaryl. The active functional groups in the starting material include, but are not limited to, any one to four selected from the group consisting of nitrogen, oxygen and sulphur, $C_3$-$C_{12}$ heterocyclyl, hydroxy, amino, and the like. The active functional groups shall be protected with inert protecting groups. In the reaction, acetonitrile is firstly dehydrogenated with strong base including, not limited to, n-butyl lithium to give negative ions. The resultant negative ions are treated with ester of compound 1 to give compound 2.

(2) Compound 8 comprising one β-carbonyl substituted acetonitrile structure and methylhydrazine or derivatives thereof are heated to form 5-aminopyrozole derivatives 9. In the step of reaction, the heating can be carried out with solvent such as alcohol, or the heating is carried out directed with methylhydrazine derivatives, wherein $R_1$ is selected from the group consisting of hydrogen, optionally substituted $C_1$-$C_{12}$ alkyl, optionally substituted $C_1$-$C_{12}$ haloalkyl, optionally substituted $C_3$-$C_{15}$ cyclic hydrocarbyl, optionally substituted $C_2$-$C_{13}$ heterocyclyl, optionally substituted $C_6$-$C_{19}$ aryl, optionally substituted $C_7$-$C_{31}$ arylalkyl and optionally substituted $C_4$-$C_{13}$ heteroaryl. The active functional groups in the starting material include, but are not limited to, any one to four selected from the group consisting of nitrogen, oxygen and sulphur, $C_3$-$C_{12}$ heterocyclyl, hydroxy, amino, and the like.

(3) Compound 9 reacts with cyclohexanone in the presence of acetic acid to give 6-aminopyrozole derivative 11. In this step of the reaction, acidic catalysts such as acetic acid, or other catalysts such as rare-earth metal can be used to catalyze the reaction, in which cyclohexanone can be substituted beforehand, such that the final compound of the present application comprises other substituents.

(4) Compound 11 reacts with ethyl isocyanate to form an adduct having relatively lower solubility at room temperature. The intermediate is heated to carry out cyclization in the pyridine or other inert solvents to give compound 12.

(5) The compound 12 is dehydrogenated with sodium hydride and then treated with silver nitrate to obtain a silver slat intermediate. The intermediate reacts with known compound 6 to give compound 13 of the present application. Alternatively, compound 12 reacts with known compound 6 in the presence of silver oxide to give compound 13 of the present application.

Finally, the protecting groups can be deprotected by a process known in the art to give a compound of the present application.

EXAMPLES

Although anyone skilled in the art is capable of preparing the compounds of the present application according to the general techniques disclosed herein above, more specific details on synthetic techniques for compounds of the present application are provided elsewhere in this specification for convenience. Again, all reagents and reaction conditions employed in synthesis are known to those skilled in the art and are available from ordinary commercial sources.

The preparation of the compounds in the present application can be performed according to, but are not limited to, the following examples.

Example 1

(2S,3S,4S,5R,6S)-6-(1,3-dimethyl-6,7,8,9-tetrahydro-3H-pyrazolo[3,4-c]isoquinoline-5-oxy)-3,4,5-trihydroxytetrahydro-2H-pyran-2-formic Acid Example 1A 1,3-dimethyl-5-amino-1H-pyrazole Under nitrogen atmosphere, to a 500 mL of round bottom flask were added 2-cyanoacetone (8 g, 0.096 mol) and 200 mL of anhydrous ethanol. 2-cyanoacetone was dissolved with stirring at room temperature. Methylhydrazine (4.43 g, 0.096 mol) was added to obtain a resultant mixture. The mixture was slowly warmed and refluxed. After reacting for 3 hr, the solvent was rotary-evaporated to obtain a product as oil. The product was purified by column chromatography to give 4.2 g of the title compound. MS (ESI): m/z 112 (M+H)$^+$ Example 1B 1,3-dimethyl-4-cyclohexenyl-5-amino-1H-pyrazole Under nitrogen atmosphere, the compound of Example 1A (2.2 g, 0.02 mol) was dissolved in 400 mL of glacial acetic acid, and cyclohexanone (3.85 g, 0.04 mol) was added to obtain a resultant mixture. The mixture was stirred homogeneously. The temperature was slowly raised to 50° C. The reaction was kept overnight. The reaction was stopped. Glacial acetic acid was rotary-evaporated to obtain a crude product. The crude product was dissolved with ethyl acetate and then was washed with aqueous solution of sodium bicarbonate. The aqueous phase was extracted twice with ethyl acetate. The organic phases were combined and dried. The solvent was rotary-evaporated. The product was purified with column chromatography (eluant: DCM:MeOH=15:1) to give 2.5 g of the title compound. MS (ESI): m/z 192 (M+H)$^+$ Example 1C 1,3-dimethyl-6,7,8,9-tetrahydro-3H-pyrazolo[3,4-c]isoquinoline-5(4H)-one Under nitrogen atmosphere, the compound of Example 1B (3 g, 15.7 mmol) was dissolved in 20 mL of pyridine at room temperature, and then ethyl isocyanate (3.34 g, 47 mmol) was added while stirring. The mixture was slowly warmed and refluxed. The reaction was kept overnight. The reaction was stopped and cooled to room temperature. Pyridine was rotary-evaporated to obtain a product as oil. After an appropriate amount of methanol was added in the product, a large amount of solids precipitated. The solids were filtered in vacuo. The resultant filter cake was washed with methanol and dried in vacuo to obtain the title compound. The filtrate was concentrated and purified by preparative thin layer chromatography (eluant: DCM:MeOH=12:1). Another portion of the title compound was given after separation. The obtained title compounds were 1.68 g in total. MS (ESI): m/z 218 (M+H)$^+$ Example 1D (2S,3S,4S,5R,6S)-3,4,5-triacetyl-6-(1,3-dimethyl-6,7,8,9-tetrahydro-3H-pyrazolo[3,4-c]isoquinoline-5-oxy)-tetrahydro-2H-pyran-2-methylformate Under nitrogen atmosphere, to a 100 mL of round bottom flask were sequentially added the compound of Example 1C (100 mg, 0.46 mmol), silver oxide (426.6 mg, 1.84 mmol), bromotriacetyl-D-methyl glucuronate (365.6 mg, 0.92 mmol) and toluene (30 mL) at room temperature. Under dark condition, the resultant mixture was slowed warmed and refluxed. The reaction was kept for 1 hr. The reaction was stopped and cooled to room temperature. Solids were filtered in vacuo. The filtrate was rotary-evaporated to dryness to obtain a product as oil. The product was separated and purified by preparative plate chromatography (eluant: DCM:MeOH=15:1) to give 162 mg of the pure title compound. MS (ESI): m/z 534 (M+H)$^+$ (2S,3S,4S,5R,6S)-6-(1,3-dimethyl-6,7,8,9-tetrahydro-3H-pyrazolo[3,4-c]isoquinoline-5-oxy)-3,4,5-trihydroxytetrahydro-2H-pyran-2-formic Acid To a 100 mL of round bottom flask were added the compound of Example 1D (180 mg, 0.34 mmol), 30 mL of THF and 8 mL of water. The temperature was kept in the range between 10° C. and 15° C. To the reaction flask was added 2 mL of alkali liquor (the process for preparing the alkali liquor: 1416 mg of LiOH.H$_2$O was exactly weighed, added into a 50 mL volumetric flask and dissolved with water, the solution was diluted to 50 mL). The reaction was kept for 2 hr. pH was adjusted with glacial acetic acid to be neutral. THF was rotary-evaporated (the temperature was kept below 30° C.). 37.0 mg of the title compound was obtained after separation and purification by HPLC. MS (ESI): m/z 394 (M+H)$^+$; $^1$H NMR (400 MHz, CD$_3$OD): δ 1.82-1.87 (m, 4 H); 2.56 (s, 3 H); 2.71 (t, J=10.4 Hz, 2 H); 3.10 (t, J=10.8 Hz, 2 H); 3.52-3.59 (m, 3 H); 3.79 (d, J=9.2 Hz, 1 H); 3.86 (s, 3 H); 6.17 (d, J=8.4 Hz, 1 H)

Example 2

(2S,3S,4S,5R,6S)-3,4,5-trihydroxy-6-(1-isopropyl-3-methyl-6,7,8,9-tetrahydro-3H-pyrazolo[3,4-c]isoquinoline-5-oxy)tetrahytho-2H-pyran-2-formic Acid Example 2A 4-methyl-3-carbonyl Valeronitrile To a 1 L of round bottom flask were added methyl isobutyrate (100 g, 0.98 mol), sodium ethoxide (66.63 g, 0.98 mol), acetonitrile (53.9 g, 0.98 mol) and 300 ml of methanol at room temperature. The resultant mixture was slowly warmed and refluxed. The reaction was kept for 6 hr. The reaction was stopped and cooled to room temperature. The solvent was rotary-evaporated. The product was distilled under reduced pressure (12 mmHg) to collect at 102-104° C. 56.2 g of the pure title compound.

Example 2B 1-methyl-3-isopropyl-5-amino-1H-pyrazole

Under nitrogen atmosphere, the compound of Example 2A (8.03 g, 72 mmol) was dissolved in alcohol (50 mL). Methylhydrazine (3.32 g, 72 mmol) was added. The resultant mixture was slowly warmed and refluxed with stirring. The reaction was kept for 3 hr. The reaction was stopped and cooled to room temperature. Alcohol was rotary-evaporated to obtain a crude product as oil. The crude product was purified with column chromatography (eluant: petroleum ether/ethyl acetate=1:1) to give 5.2 g of the title compound. MS (ESI): m/z 140 (M+H)$^+$ Example 2C 1-methyl-3-isopropyl-4-cyclohexenyl-5-amino-1H-pyrazole Under nitrogen atmosphere, to a 100 mL of round bottom flask were added the compound of Example 2B (5.2 g, 38 mmol) and 40 mL of glacial acetic acid. After the compound was dissolved with stirring, cyclohexanone (8.22 g, 76 mmol) was added. The resultant mixture was warmed to 50° C. The reaction was kept overnight. The reaction was stopped. Glacial acetic acid was rotary-evaporated. The resultant product was dissolved with ethyl acetate and washed to alkalescence with aqueous solution of sodium bicarbonate. The ethyl acetate layer was separated. The aqueous layer was extracted twice with ethyl acetate. The organic layers were combined and dried over MgSO$_4$. The solvent was rotary-evaporated. The product was purified with column chromatography (eluant: petroleum ether:ethyl acetate=1:1) to give 4.5 g of the title compound. MS (ESI): m/z 220 (M+H)$^+$ Example 2D 1-isopropyl-3-methyl-6,7,8,9-tetrahydro-3H-pyrazolo[3,4-c]isoquinoline-5(4H)-one Under nitrogen atmosphere, the compound of Example 2C (0.5 g, 2.3 mmol) was dissolved in 20 mL of pyridine. Ethyl isocyanate (0.522 g, 4.6 mmol) was added with stirring. The resultant mixture was slowly warmed and refluxed. The reaction was kept overnight. The reaction was stopped and cooled to room temperature. Pyridine was rotary-evaporated to obtain a product as oil. After an appropriate amount of methanol was added, a large amount of solids precipitated. The solids were filtered in vacuo. The resultant filter cake was washed with methanol and dried in vacuo to give the title compound. The filtrate was concentrated and purified by preparative thin layer chromatography (eluant: DCM:MeOH=18:1). Another portion of the title compound was given after separation. The obtained title compounds were 408 mg in total. MS (ESI): m/z 246 (M+H)$^+$ Example 2E (2S,3S,4S,5R,6S)-3,4,5-triacetyl-6-(1-isopropyl-3-methyl-6,7,8,9-tetrahydro-3H-pyrazolo[3,4-c]isoquinoline-5-oxy)-tetrahydro-2H-pyran-2-methylformate Under nitrogen atmosphere, to a 100 mL of round bottom flask were added the compound of Example 2D (100 mg, 0.41 mmol), silver oxide (377.85 mg, 1.64 mmol), bromotriacetyl-D-methyl glucuronate (323.8 mg, 0.82 mmol) and toluene (30 mL). The reaction flask was kept in dark. The resultant mixture was slowly warmed and refluxed. The reaction was kept for 40 min. The reaction was stopped and cooled to room temperature. The solids in the reaction solution were filtered in vacuo. The filter cake was washed twice with toluene. The filtrates were combined. The solvent was rotary-evaporated to obtain a product as oil. The product was separated and purified by HPLC to give 187 mg of the titled compound. MS (ESI): m/z 562 (M+H)$^+$ (2S,3S,4S,5R,6S)-3,4,5-trihydroxy-6-(1-isopropyl-3-methyl-6,7,8,9-tetrahydro-3H-pyrazolo[3,4-c]isoquinoline-5-oxy)tetrahydro-2H-pyran-2-formic Acid To a 100 mL of round bottom flask were added the compound of Example 2E (187 mg, 0.33 mmol), 30 mL of THF and 8 mL of water. The temperature was kept in the range between 10° C. and 15° C. To the reaction flask was added 2 mL of alkali liquor (the process for preparing the alkali liquor: 1,416 mg of LiOH.H$_2$O was exactly weighed, added into a 50 mL volumetric flask and dissolved with water, the solution was diluted to 50 mL). The reaction was kept for 2 hr. pH was adjusted with glacial acetic acid to be neutral. THF was rotary-evaporated (the temperature was kept below 30° C.). 62 mg of the title compound was given after separation and purification by HPLC. MS (ESI): m/z 421 (M+H)$^+$; $^1$H NMR (400 MHz, CD$_3$OD): δ 1.35 (d, J=6.8 Hz, 6 H); 1.84-1.85 (m, 4 H); 2.74-2.80 (m, 2 H); 3.10-3.12 (m, 2 H); 3.50-3.53 (m, 1 H); 3.55-3.58 (m, 3 H); 3.80 (d, J=9.2 Hz, 1 H); 3.89 (s, 3 H); 6.18 (d, J=8.0 Hz, 1 H)

Example 3

(2S,3S,4S,5R,6S)-3,4,5-trihydroxy-6-(1-phenyl-3-methyl-6,7,8,9-tetrahydro-3H-pyrazolo[3,4-c]isoquinoline-5-oxy)-tetrahydro-2H-pyran-2-formic Acid Example 3A 1-methyl-3-phenyl-4-cyclohexenyl-5-amino-1H-pyrazole Under nitrogen atmosphere, to a 100 mL of round bottom flask were added 1-methyl-3-phenyl-5-amino-1-hydro-pyrozole (5 g, 28 mmol) and 40 mL of glacial acetic acid. 1-methyl-3-phenyl-5-amino-1-hydro-pyrozole was dissolved with stirring. Cyclohexanone (5.6 g, 57 mmol) was added to obtain a resultant mixture. The mixture was warmed to 50° C. with stirring. The reaction was kept warm overnight. The reaction was stopped. The solvent was rotary-evaporated. An appropriate amount of ethyl acetate was added. The mixture was washed to be natural with aqueous solution of sodium bicarbonate. The ethyl acetate layer was separated. The aqueous layer was extracted twice with ethyl acetate. The organic layers were combined. The combined organic phase was dried over MgSO$_4$. The solvent was rotary-evaporated. The crude product was purified by column chromatography to give 4.4 g of the pure title compound. Yield: 54.26%. MS (ESI): m/z 254 (M+H)$^+$ Example 3B 1-phenyl-3-methyl-6,7,8,9-tetrahydro-3H-pyrazolo[3,4-c]isoquinoline-5(4H)-one The compound of Example 3A (2 g, 8 mmol) and ethyl isocyanate (1.67 g, 24 mmol) were dissolved in pyridine (30 mL) at room temperature. The mixture was warmed, refluxed and stirred overnight. The reaction was stopped. The solvent was rotary-evaporated. A small amount of ethanol was added. A large amount of solids were precipitated. The solids were filtered in vacuo. The solvent was rotary-evaporated. The residue was purified by column chromatography to give 1.618 g of the pure title compound. MS (ESI): m/z 280 (M+H)$^+$ Example 3C (2S,3S,4S,5R,6S)-3,4,5-triacetyl-6-(3-methyl-1-phenyl-6,7,8,9-tetrahydro-3H-pyrazolo[3,4-c]isoquinoline-5-oxy)-tetrahydro-2H-pyran-2-methylformate Under nitrogen atmosphere, to a 100 mL of round bottom flask were added bromotriacetyl-D-methyl glucuronate (850 mg, 2.2 mmol), silver oxide (1 g, 4 eq), the compound of Example 3B (300 mg, 1.1 mmol) and toluene (30 mL). The mixture was stirred homogenously. The reaction flask was kept in dark, warmed and refluxed. The reaction was kept for 1 hr. The reaction was stopped and cooled to room temperature. The solids were filtered in vacuo. The filter cake was washed twice with toluene. After the filtrates were combined, the solvent was rotary-evaporated. The crude product was purified by column chromatography (eluant: DCM:MeOH=25:1) to give 450 mg of the title compound. MS (ESI): m/z 596 (M+H)$^+$ (2S,3S,4S,5R,6S)-3,4,5-trihydroxy-6-(1-phenyl-3-methyl-6,7,8,9-tetrahydro-3H-pyrazolo[3,4-c]isoquinoline-5-oxy)-tetrahydro-2H-pyran-2-formic Acid The compound of Example 3C (450 mg, 0.76 mmol) was dissolved in 40 ml of THF. 6 mL of water was added (the temperature was kept in the range between 15° C. and 20° C.). 4 mL of alkali liquor (the process for preparing the alkali liquor: 1.585 g of LiOH.H$_2$O was weighed, added into a 50 mL volumetric flask, and diluted with water to the mark) was added. The reaction was stirred for 1 hr. The reaction was stopped. The mixture was adjusted with acetic acid to be neutral. The solvent was rotary-evaporated (the temperature was kept below 30° C.). The product was separated and purified by HPLC to give 160 mg of the title compound as white solid. Yield: 46.5%. MS (ESI): m/z 456 (M+H)$^+$; $^1$H NMR (400 MHz, CD$_3$OD): δ 1.56-1.58 (m, 2 H); 1.71-1.72 (m, 2 H); 2.55-2.57 (m, 2 H); 2.58-2.61 (m, 2 H); 3.45-3.51 (m, 3 H); 3.74 (d, J=9.6 Hz, 1 H); 3.91 (s, 3 H); 6.13 (d, J=8.4 Hz, 1 H); 7.35 (t, J=3.2 Hz, 1 H); 7.37-7.38 (m, 2 H); 7.44-7.46 (m, 2 H)

Example 4

(2S,3S,4S,5R,6S)-3,4,5-trihydroxy-6-(3-methyl-1-((R)-1-propylpyrrolidin-2-yl)-6,7,8,9-tetrahydro-3H-pyrazolo[3,4-c]isoquinoline-5-oxy)tetrahydro-2H-pyran-2-formic Acid

Example 4A (R)—N-benzyloxycarbonylmethylprolinate

To a 1000 mL of reaction flask were added oxalyl chloride (38.07 g, 300 mmol), benzene (350 mL), (R)—N-Cbz-proline (62.30 g, 250 mmol) and DMF (6 drops). The reaction was kept with stirring for 3 hr at room temperature. Methanol (350 mL) was added. The reaction was further kept with stirring for 1 hr. The reaction was stopped. The solvent was rotary-evaporated. Ethyl acetate (400 mL) was added. The resultant mixture was sequentially washed with saturated NaHCO$_3$ solution and saturation NaCl solution. The product was dried over anhydrous Na$_2$SO$_4$. 65.51 g of the title compound as pale yellow liquid were given after concentration. Yield: 99.5%

Example 4B (R)-2-(2-cyanoacetyl)pyrrolidine-1-benzyl Formate

Under nitrogen atmosphere, to a 1000 mL of reaction flask were added dried acetonitrile (15.54 mL, 298.6 mmol) and anhydrous THF (350 mL). The mixture was cooled to −78° C. To the mixture was slowly added n-butyl lithium (171 mL, 1.6 mol/L, 273.7 mmol). The resultant mixture reacted with stirring for 30 min at −78° C. A solution of the compound of Example 4A (65.51 g, 248.8 mmol) in THT (100 mL) was added. The reaction was further kept for 1 hr at −78° C. Then, the reaction was warmed to −20° C. for 30 min, and finally warmed to room temperature for 30 min. The reaction was stopped. Ethyl ether (100 mL) was added to the reaction system to dilute. Water (100 mL) was added for quenching the reaction. pH was adjusted with diluted hydrochloric acid to 3. The organic phase was washed with saturated saline, dried and concentrated. The concentrated organic phase was separated by column chromatography to give 59.5 g of the title compound as pale yellow liquid. Yield: 87.8%. MS (ESI): m/z 273 (M+H)$^+$

Example 4C (R)-2-(5-amino-1-methyl-1H-pyrazol-3-yl)pyrrolidine-1-benzyl Formate To a 500 mL of reaction flask were added Example 4B (59.5 g, 218.51 mmol) anhydrous ethanol (300 mL) and methylhydrazine (18 mL, 327.76 mmol). The mixture was heated to reflux under nitrogen atmosphere. The reaction was kept for 3 hr. The reaction was stopped. The solvent was rotary-evaporated to obtain a crude product. The crude product was separated by column chromatography to give 47.86 g of the title compound as yellow solid. Yield: 72.9%. MS (ESI): m/z 301 (M+H)$^+$

Example 4D (R)-2-(5-amino-4-cyclohexenyl-1-methyl-1H-pyrazol-3-yl)pyrrolidine-1-benzyl Formate To a 500 mL of reaction flask were added the compound of Example 4C (47.86 g, 159.32 mmol), cyclohexanone (31.27 g, 318.64 mmol) and acetic acid (300 mL). The mixture was heated to 50° C. to 60° C. under nitrogen atmosphere. The reaction was kept overnight. The reaction was stopped and cooled to room temperature. Acetic acid was rotary-evaporated to obtain a crude product. The crude product was separated by column chromatography to give 45.53 g of the title compound as white solid. Yield: 75.1%. MS (ESI): m/z 381 (M+H)$^+$

Example 4E (R)-2-(3-methyl-5-oxy-4,5,6,7,8,9-hexahydro-3H-pyrazolo[3,4-c]isoquinolin-1-yl)pyrrolidin-1-benzyl Formate To a 500 mL of reaction flask were added the compound of Example 4D (27.2 g, 71.48 mmol), ethyl isocyanate (15.24 g, 214.45 mmol) and pyridine (150 mL). The reaction was kept overnight with refluxing under nitrogen atmosphere. The reaction was stopped and cooled to room temperature. The product was concentrated by rotary-evaporation. Methanol was added. After the mixture was kept standing, solids precipitated. The solids were filtered in vacuo to give 15.2 g of the title compound. Yield: 52.3%. MS (ESI): m/z 407 (M+H)$^+$

Example 4F (R)-3-methyl-1-(pyrrolidin-2-yl)-6,7,8,9-tetrahydro-3H-pyrazolo[3,4-c]isoquinoline-5(4H)-one To a single reaction flask was added 0.2 g of 10% Pd/C. Then a solution of the compound of Example 4E (1.2 g) in a mixture of methanol (30 mL) and dichloromethane (30 mL) was added under nitrogen atmosphere. Hydrogen was injected. The mixture was stirred overnight at room temperature. The resultant product was filtered in vacuo. The mother liquid was concentrated to give the title compound. Yield: 100%. MS (ESI): m/z 273 (M+H)$^+$

Example 4G (R)-3-methyl-1-(1-propylpyrrolidin-2-yl)-6,7,8,9-tetrahydro-3H-pyrazolo[3,4-c]isoquinoline-5(4H)-one To a 250 mL of reaction flask were added the compound of Example 4F (1.39 g, 5.1 mmol), propanal (0.888 g, 15.31 mmol) and methanol (90 mL). The mixture was stirred for 2 hr at room temperature. Sodium cyanoborohydride (1.0 g, 15.9 mmol) was added to the mixture. The reaction was kept overnight with stirring. The reaction was stopped. The product was concentrated by rotary-evaporation and purified by column chromatography to give 1.4 g of the title compound. Yield: 87.5%. MS (ESI): m/z 315 (M+H)$^+$

Example 4H (2S,3S,4S,5R,6S)-3,4,5-triacetyl-6-(3-methyl-1-((R)-1-propylpyrrolidin-2-yl)-6,7,8,9-tetrahydro-3H-pyrazolo[3,4-c]isoquinoline-5-oxy)-tetrahydro-2H-pyran-2-methylformate To a 250 mL of reaction flask were added the compound of Example 4G (0.5 g, 1.59 mmol), bromotriacetyl-D-methyl glucuronate (1.31 g. 3.18 mmol), silver oxide (1.47 g, 6.36 mmol) and toluene (125 mL). The mixture was refluxed for 2 hr. The reaction was stopped and cooled to room temperature. The silver oxide was filtered in vacuo. The mother liquid was concentrated by rotary-evaporation to remove toluene so as to obtain a crude product. The crude product was subject to column chromatography (eluant: dichloromethane:methanol=10:1) to give 0.7 g of the title compound. Yield: 70%. MS (ESI): m/z 631 (M+H)$^+$ (2S,3S,4S,5R,6S)-3,4,5-trihydroxy-6-(3-methyl-1-(R)-1-propylpyrrolidin-2-yl)-6,7,8,9-tetrahydro-3H-pyrazolo[3,4-c]isoquinoline-5-oxy)tetrahydro-2H-pyran-2-formic Acid To a 100 mL of reaction flask were added the compound of Example 4H (0.26 g, 0.41 mmol), tetrahydrofuran (25 mL), water (4 mL) and an aqueous solution of lithium hydroxide (2 mL) (preparation process: 1.72 g of lithium hydroxide monohydrate was weighed and dissolved in 50 mL of water). The reaction was kept for 2 hr at room temperature. The reaction was stopped. pH was adjusted with acetic acid to of 6-7. The solvent was removed by rotary-evaporation. The product was separated and purified by HPLC to give 30 mg of the title compound. MS (ESI): m/z 491 (M+H)$^+$; $^1$H NMR (400 MHz, CD$_3$OD): δ 0.90 (t, J=7.6 Hz, 3 H); 1.60-1.66 (m, 2 H); 1.85-1.86 (m, 4 H); 2.04-2.11 (m, 1 H); 2.13-2.16 (m, 1 H); 2.17-2.19 (m, 1 H); 2.57-2.69 (m, 2 H); 2.73-2.79 (m, 1 H); 2.91-2.93 (m, 1 H); 2.98-3.02 (m, 1 H); 3.05-3.07 (m, 1 H), 3.09-3.13 (m, 2 H); 3.51-3.60 (m, 3 H); 3.76-3.78 (m, 1 H); 3.79-3.80 (m, 1 H); 3.97 (s, 3 H); 4.83 (t, J=4.0 Hz, 1 H); 6.16 (d, J=8.0 Hz, 1 H)

Example 5

(2S,3S,4S,5R,6S)-3,4,5-trihydroxy-6-(3-methyl-1-((S)-1-propylpyrrolidin-2-yl)-6,7,8,9-tetrahydro-3H-pyrazolo[3,4-c]isoquinoline-5-oxy)tetrahydro-2H-pyran-2-formic Acid The compound of Example 5 was prepared with similar experimental procedures and methods to those in Example 4A except that Cbz-R-proline in Example 4A was replaced with Cbz-S-proline. MS (ESI): m/z 491 (M+H)$^+$; $^1$H NMR (400 MHz, CD$_3$OD): δ 0.93 (t, J=7.2 Hz, 3 H); 1.63-1.71 (m, 2 H); 1.84-1.88 (m, 4 H); 2.14-2.17 (m, 1 H); 2.19-2.23 (m, 1 H); 2.25-2.29 (m, 1 H); 2.65-2.68 (m, 2 H); 2.70-2.74 (m, 1 H); 2.95-3.01 (m, 1 H); 3.04-3.05 (m, 1 H); 3.06-3.09 (m, 1 H), 3.10-3.25 (m, 2 H); 3.51-3.61 (m, 3 H); 3.78-3.79 (d, J=2 Hz, 1 H); 3.84-3.85 (m, 1 H); 3.86 (s, 3 H); 5.05 (t, J=7.6 Hz, 1 H); 6.15 (d, J=7.6 Hz, 1 H)

Example 6

(2S,3S,4S,5R,6S)-3,4,5-trihydroxy-6-(3-methyl-1-(1-propylpyrrolidin-3-yl)-6,7,8,9-tetrahydro-3H-pyrazolo[3,4-c]isoquinoline-5-oxy)tetrahydro-2H-pyran-2-formic Acid The compound of Example 6 was prepared with similar experimental procedures and methods to those in Example 4A except that Cbz-R-proline in Example 4A was replaced with Cbz-3-pyrrole carboxylic acid0. MS (ESI): m/z 491 (M+H)$^+$; $^1$H NMR (400 MHz, CD3OD): δ 1.06 (t, J=7.2 Hz, 3 H); 1.75-1.89 (m, 6 H); 2.14-2.22 (m, 1 H); 2.46-2.55 (m, 1 H); 2.62-2.84 (m, 2 H); 2.96-3.02 (m, 2 H); 3.06-3.16 (m, 2 H); 3.40-3.48 (m, 1 H); 3.58-3.64 (m, 3 H); 3.84-3.88 (m, 1 H); 3.89 (s, 3 H), 3.92-3.94 (m, 0.5 H); 3.99-4.07 (m, 1 H); 4.30-4.36 (m, 0.5 H); 4.61-4.69 (m, 1 H); 6.15 (d, J=7.2 Hz, 1 H)

Example 7

(2S,3S,4S,5R,6S)-3,4,5-trihydroxy-6-(3-methyl-1-(1-ethylpyrrolidin-3-yl)-6,7,8,9-tetrahydro-3H-pyrazolo[3,4-c]isoquinoline-5-oxy)tetrahydro-2H-pyran-2-formic Acid

Example 7A 1-(3-pyrrolyl)-3-methyl-6,7,8,9-tetrahydropyrazolo[3,4-c]isoquinoline-5-one The compound of Example 7A was prepared with similar experimental procedures and methods to those in Examples 4A-4F except that Cbz-R-proline in Example 4A was replaced with Cbz-3-pyrrole carboxylic acid. MS (ESI): m/z 273 (M+H)$^+$

Example 7B 1-(1-ethyl-3-pyrrolyl)-3-methyl-6,7,8,9-tetrahydro-pyrazolo[3,4-c]isoquinoline-5-one Under nitrogen atmosphere, to a 250 mL of reaction flask were added the compound of Example 7A (0.2 g, 0.7 mmol), sodium cyanoborohydride (0.13 g, 2.1 mmol), zinc chloride (0.2 g, 1.47 mmol) and methanol (50 mL). The mixture was stirred for several minutes at room temperature. Freshly distilled ethanal (0.097 g, 2.2 mmol) was added to the mixture and stirred for 2 hr. After the reaction completed, pH was adjusted with hydrochloric acid, to 2-3. The product was concentrated to remove methanol and water, and purified by preparative silica gel to give 200 mg of the title compound as white solid. Yield: 91.3%. MS (ESI): m/z 301 (M+1, 100%); 302 (M+2, 60%); 303 (M+3, 10%); $^1$HNMR (400 MHz, CDCl$_3$): δ 1.43 (t, J=7.2 Hz, 3 H); 1.78-1.84 (m, 4 H); 2.15-2.22 (m, 1 H); 2.54-2.59 (m, 2 H); 2.60-2.61 (m, 1 H); 2.82-2.98 (m, 4 H); 3.14-3.15 (m, 2 H); 3.60-3.63 (m, 1 H); 3.80-3.84 (m, 1 H); 3.97 (s, 3 H)

(2S,3S,4S,5R,6S)-3,4,5-trihydroxy-6-(3-methyl-1-(1-ethylpyrrolidin-3-yl)-6,7,8,9-tetrahydro-3H-pyrazolo[3,4-c]isoquinoline-5-oxy)tetrahydro-2H-pyran-2-formic Acid The compound of Example 7 was prepared with similar experimental procedures and methods to those in Examples 4H and 4 except that the starting material Example 4G in Example 4H was replaced with the compound of Example 7B. MS (ESI): m/z 477 (M+1, 100%); $^1$H NMR (400 MHz, CDCl$_3$): δ 1.12-1.16 (m, 3 H); 1.71-1.79 (m, 4 H); 2.05-2.33 (m, 3 H); 2.53-2.82 (m, 6 H); 2.89-2.96 (m, 3 H); 2.99-3.02 (m, 2 H); 3.24 (m, 2 H); 3.44-3.50 (m, 3 H); 3.70-3.73 (m, 1 H); 3.80 (d, J=4.0 Hz, 3 H); 4.40-4.45 (m, 1 H); 6.05-6.08 (m, 1 H)

Example 8

(2S,3S,4S,5R,6S)-3,4,5-trihydroxy-6-(3-methyl-1-(1-(3,3,3-trifluoropropyl)pyrrolidin-3-yl)-6,7,8,9-tetrahydro-3H-pyrazolo[3,4-c]isoquinoline-5-oxy)tetrahydro-2H-pyran-2-formic Acid

Example 8A 1-(1-3,3,-trifluoropropyl-3-pyrrolyl)-3-methyl-6,7,8,9-tetrahydropyrazolo[3,4-c]isoquinoline-5-one Under nitrogen atmosphere, to a 250 mL of reaction flask were added the compound of Example 7A (0.2 g, 0.73 mmol), sodium cyanoborohydride (0.14 g, 2.2 mmol), zinc chloride (0.2 g, 1.47 mmol) and methanol (50 mL). The mixture was stirred for several minutes at room temperature. 3,3,3-trifluoropropanal (0.25 g, 2.2 mmol) was added and stirred for 2 hr. After the reaction completed, pH was adjusted with hydrochloric acid to 2-3. The product was concentrated to remove methanol and water, and purified by preparative silica gel to give 238.1 mg of the title compound as white solid. Yield: 88.6%. MS (ESI): m/z 369 (M+1, 100%); $^1$H NMR (400 MHz, CDCl$_3$): δ 1.76-1.87 (m, 4 H); 2.16-2.26 (m, 1 H); 2.27-2.45 (m, 3 H); 2.51-2.52 (m, 2 H); 2.64-2.70 (m, 1 H); 2.71-2.80 (m, 1 H); 2.83-2.98 (m, 5 H); 3.01-3.02 (m, 1 H); 3.75-3.83 (m, 1 H); 4.01 (s, 3 H)

(2S,3S,4S,5R,6S)-3,4,5-trihydroxy-6-(3-methyl-1-(1-(3,3,3-trifluoropropyl)pyrrolidin-3-yl)-6,7,8,9-tetrahydro-3H-pyrazolo[3,4-c]isoquinoline-5-oxy)tetrahydro-2H-pyran-2-formic Acid The compound of Example 8 was prepared with similar experimental procedures and methods to those in Examples 4H and 4 except that the starting material Example 4G in Example 4H was replaced with to the compound of Example 8A. MS (ESI): m/z 545 (M+1, 100%); MS (ESI): m/z 545 (M+1, 100%); $^1$H NMR (400 MHz, D$_2$O): δ 1.80-1.81 (m, 4 H); 2.22-2.24 (m, 2 H); 2.32-2.41 (m, 4 H); 2.62-2.68 (m, 5 H); 2.76-2.83 (m, 1 H); 2.83-2.87 (m, 2 H); 3.04-3.12 (m, 1 H); 3.52-3.63 (m, 3 H); 3.90 (s, 3 H); 5.04-5.08 (m, 1 H); 6.15 (d, J=7.6 Hz, 1 H)

Example 9

(2S,3S,4S,5R,6S)-3,4,5-trihydroxy-6-(3-methyl-1-((R)-1-propylpyrrolidin-3-yl)-6,7,8,9-tetrahydro-3H-pyrazolo[3,4-c]isoquinoline-5-oxy)tetrahydro-2H-pyran-2-formic Acid

Example 9A (2S,3S,4S,5R,6S)-3,4,5-triacetyl-6-(3-methyl-1-(1-propylpyrrolidin-3-yl)-6,7,8,9-tetrahydro-3H-pyrazolo[3,4-c]isoquinoline-5-oxy)-tetrahydro-2H-pyran-2-methylformate The compound of Example 9A was prepared with similar experimental procedures and methods to those in Example 4H except that Cbz-R-proline in Example 4A was replaced with Cbz-3-pyrrole carboxylic acid. MS (ESI): m/z 631 (M+H)$^+$

Example 9B (2S,3S,4S,5R,6S)-3,4,5-triacetyl-6-(3-methyl-1-((R)-1-propylpyrrolidin-3-yl)-6,7,8,9-tetrahydro-3H-pyrazolo[3,4-c]isoquinoline-5-oxy)-tetrahydro-2H-pyran-2-methylformate The compound of Example 9A was separated by preparative HPLC equipped with chiral chromatographic column (the chromatographic column type and the separation conditions: chiral preparative column-Chiralpak AD-H, 25 cm×3 cm, flow rate: 12 mL/min, wavelength: 220 nm, column temperature: 40° C., mobile phase: ethanol:diethylamine=100:0.1), to provide a component with less polarity (retention time: 12 min). The product was concentrated to give the title compound Example 9B. MS (ESI): m/z 631 (M+H)$^+$ (2S,3S,4S,5R,6S)-3,4,5-trihydroxy-6-(3-methyl-1-((R)-1-propylpyrrolidin-3-yl)-6,7,8,9-tetrahydro-3H-pyrazolo[3,4-c]isoquinoline-5-oxy)tetrahydro-2H-pyran-2-formic Acid The compound of Example 9 was prepared with similar experimental procedures and methods to those in Example 4 except that the starting material Example 4H in Example 4 was replaced with the compound of Example 9B. Yield 92.6%. MS (ESI): m/z 491 (M+1, 100%); $^1$H NMR (400 MHz, D$_2$O): δ 0.80 (t, J=7.2 Hz, 3 H); 1.52-1.58 (m, 6 H); 2.04-2.13 (m, 1 H); 2.31-2.43 (m, 3 H); 2.66-2.68 (m, 2 H); 2.92-2.97 (m, 2 H); 3.17-3.25 (m, 2 H); 3.29-3.34 (m, 1 H); 3.43-3.55 (m, 4 H); 3.07 (s, 3 H); 3.80-3.87 (m, 2 H), 5.96 (d, J=6.8 Hz, 1 H)

Example 10

(2S,3S,4S,5R,6S)-3,4,5-trihydroxy-6-(3-methyl-1-((S)-1-propylpyrrolidin-3-yl)-6,7,8,9-tetrahydro-3H-pyrazolo[3,4-c]isoquinoline-5-oxy)tetrahydro-2H-pyran-2-formic Acid

Example 10A (2S,3S,4S,5R,6S)-3,4,5-triacetyl-6-(3-methyl-1-((S)-1-propylpyrrolidin-3-yl)-6,7,8,9-tetrahydro-3H-pyrazolo[3,4-c]isoquinoline-5-oxy)-tetrahydro-2H-pyran-2-methylformate The compound of Example 9A was separated by preparative HPLC equipped with chiral chromatographic column (the chromatographic column type and the separation conditions: chiral preparative column-Chiralpak AD-H, 25 cm×3 cm, flow rate: 12 mL/min, wavelength: 220 nm, column temperature: 40° C., mobile phase: ethanol:diethylamine=100:0.1) to provide a component with more polarity (retention time: 19 min). The product was concentrated to give the title compound Example 10A MS (ESI): m/z 631 (M+H)$^+$ (2S,3S,4S,5R,6S)-3,4,5-trihydroxy-6-(3-methyl-1-((S)-1-propylpyrrolidin-3-yl)-6,7,8,9-tetrahydro-3H-pyrazolo[3,4-c]isoquinoline-5-oxy)tetrahydro-2H-pyran-2-formic Acid The compound of Example 10 was prepared with similar experimental procedures and methods to those in Example 4 except that the starting material Example 4H in Example 4 was replaced with the compound of Example 10A. Yield: 90%. MS (ESI): m/z 491 (M+1, 100%); $^1$H NMR (400 MHz, D₂O): δ 0.84 (t, J=7.6 Hz, 3 H); 1.55-1.65 (m, 6 H); 1.95-2.02 (m, 1 H); 2.32-2.39 (m, 3 H); 2.61-2.66 (m, 2 H); 3.02-3.10 (m, 2 H); 3.24-3.39 (m, 2 H); 3.41-3.58 (m, 5 H); 3.65 (s, 3 H); 3.80 (d, J=9.6 Hz, 1 H); 3.86-3.92 (m, 1 H); 5.95 (d, J=7.2 Hz, 1 H)

Example 11

(2S,3S,4S,5R,6S)-3,4,5-trihydroxy-6-(1-(1-ethylpiperidin-2-yl)-3-methyl-6,7,8,9-tetrahydro-3H-pyrazolo[3,4-c]isoquinoline-5-oxy)tetrahydro-2H-pyran-2-formic Acid

Example 11A 2-(2-cyanoacetyl)piperidine-1-benzyl Formate

To a 250 mL of three-neck flask was added dried acetonitrile (5.01 g, 122 mmol). To the flask was added anhydrous THF (187 mL) under nitrogen atmosphere. The flask was cooled to −78° C. To the flask was added n-butyl lithium (70.6 mL, 113 mmol) in batch. After adding, the mixture was stirred for 1 hr under this temperature. A solution of N-Cbz-piperidine-2-methylformate (24.1 g, 87 mmol) in anhydrous THF (70 mL) was further added in batch. The mixture reacted for further 45 min at −78° C. The mixture was naturally warmed to room temperature and quenched with water. The mixture was rotary-evaporated to remove THF. 600 mL of water was added. The impurities were removed by extraction with 100 mL of ethyl ether. pH of the aqueous layer was adjusted with diluted hydrochloric acid to 7 to 8. The aqueous layer was extracted with dichloromethane. The combined organic phase was dried over anhydrous Na₂SO₄. The mother liquid was concentrated after being filtered in vacuo so as to give 16.0 g of the title compound. Yield: 64.3%. MS (ESI): m/z 287 (M+H)⁺

Example 11B 2-(1-methyl-5-amino-1H-pyrazol-3-yl)piperidine-1-benzyl Formate

Under nitrogen atmosphere, to a 250 mL three-neck reaction flask were added the compound of Example 11A (16.0 g, 55.9 mmol), ethanol (80 mL) and methylhydrazine (12 mL, 224 mmol). The mixture was refluxed for 5 hr. The reaction was stopped. Ethanol was removed by rotary-evaporation to obtain a crude product. The crude product was subject to column chromatography (eluant: petroleum ether:ethyl acetate=1:1) to give 11.7 g of the title compound. Yield: 66.6%. MS (ESI): m/z 315 (M+H)⁺

Example 11C 2-(1-methyl-4-cyclohexenyl-5-amino-1H-pyrazol-3-yl)piperidine-1-benzyl Formate Under nitrogen atmosphere, to a 250 mL three-neck reaction flask were added the compound of Example 11B (11.7 g, 37 mmol), ethanol (150 mL) and cyclohexanone (15.5 mL, 149 mmol). The mixture reacted overnight at 50° C. to 60° C. After cooled to room temperature, acetic acid was removed by rotary-evaporation to obtain a crude product. The crude product was subject to column chromatography (eluant: petroleum ether:ethyl acetate=2:1) to give 8.0 g of the title compound. Yield: 54.4%. MS (ESI): m/z 395 (M+H)⁺

Example 11D 2-(3-methyl-5-oxy-4,5,6,7,8,9-hexahydro-3H-pyrazolo[3,4-c]isoquinolin-1-yl)piperdin-1-benzyl Formate Under nitrogen atmosphere, to a 250 mL of reaction flask were added the compound of Example 11C (8.0 g, 20.3 mmol), ethyl isocyanate (8 mL, 101.4 mmol) and pyridine (60 mL). The mixture was refluxed overnight. The reaction was cooled to room temperature. Pyridine was removed by rotary-evaporation. Ethanol was added to recrystallize. Solids were filtered in vacuo to give 6.1 g of the title compound as white. Yield: 71.5%. MS (ESI): m/z 421 (M+H)⁺

Example 11E 3-methyl-1-(piperidin-2-yl)-6,7,8,9-tetrahydro-3H-pyrazolo[3,4-c]isoquinoline-5(4H)-one Under nitrogen atmosphere, to a single flask containing 0.2 g of 10% Pd/C was added a solution of Example 11D (1.2 g, 2.85 mmol) in a mixture of dichloromethane (30 mL) and methanol (30 mL). Hydrogen was injected. The reaction was stirred overnight at room temperature. Solids were filtered in vacuo. The filtrate was concentrated to give the title compound. Yield: 100%. MS (ESI): m/z 287 (M+H)⁺

Example 11F 1-(1-ethylpiperidin-2-yl)-3-methyl-6,7,8,9-tetrahydro-3H-pyrazolo[3,4-c]isoquinoline-5(4H)-one Under nitrogen atmosphere, to a 250 mL of reaction flask were added the compound of Example 11E (0.8172 g, 2.85 mmol), aldehyde (0.377 g, 8.56 mmol) and methanol (100 mL). The mixture reacted under stirring for 2 hr at room temperature. Then sodium cyanoborohydride (0.54 g, 8.56 mmol) was added to the mixture. The reaction was kept under stirring overnight. The reaction was stopped. The mixture was rotary-evaporated to remove methanol to obtain a crude product. The crude product was subject to column chromatography (eluant: dichloromethane:methanol=10:1) to give 0.79 g of the title compound as white solid. Yield: 88.1%. MS (ESI): m/z 315 (M+H)⁺

Example 11G (2S,3S,4S,5R,6S)-3,4,5-triacetyl-6(1-(1-ethylpiperidin-2-yl)-3-methyl-6-,7,8,9-tetrahydro-3H-pyrazolo[3,4-c]isoquinoline-5-oxy)tetrahydro-2H-pyran-2-methylformate To a 250 mL of reaction flask were added the compound of Example 11F (0.5 g, 1.59 mmol), bromotriacetyl-D-methyl glucuronate (1.31 g, 3.18 mmol), silver oxide (1.47 g, 6.36 mmol) and toluene (125 mL). The mixture was refluxed for 3 hr. The reaction was stopped. Silver oxide was filtered in vacuo. The filtrate was concentrated by rotary-evaporation to remove toluene. The product was subject to column chromatography (eluant: dichloromethane:methanol=10:1) to give 0.7 g of the title compound. Yield: 70%. MS (ESI): m/z 631 (M+H)⁺

(2S,3S,4S,5R,6S)-3,4,5-trihydroxy-6-(1-(1-ethylpiperidin-2-yl)-3-methyl-6,7,8,9-tetrahydro-3H-pyrazolo[3,4-c]isoquinoline-5-oxy)tetrahydro-2H-pyran-2-formic Acid To a 100 mL reaction flask were added the compound of Example 11G (200 mg, 316.1 mmol), tetrahydrofuran (25 mL) and water (4 mL). An aqueous solution of lithium hydroxide (4 mL) (preparation process: 1.3264 g of lithium hydroxide monohydrate was weighed and dissolved in 50 mL of water). The mixture reacted for 2 hr at room temperature. The reaction was stopped. pH was adjusted with acetic acid to 6-7. The mixture was rotary-evaporated to remove THF at room temperature. The product was subject to HPLC to give 63 mg of the title compound. MS (ESI): m/z 491 (M+H)$^+$; $^1$H NMR (400 MHz, CD$_3$OD): δ 1.09 (t, J=7.2 Hz, 3 H); 1.39-1.49 (m, 1 H); 1.62-1.70 (m, 2 H); 1.75-1.78 (m, 2 H); 1.79-1.83 (m, 2 H); 1.87-1.93 (m, 2 H); 2.00-2.12 (m, 1 H); 2.57-2.63 (m, 2 H); 2.64-2.70 (m, 1 H); 2.89-3.00 (m, 3 H); 3.02-3.07 (m, 1 H), 3.41-3.53 (m, 3 H); 3.62 (d, J=8.0 Hz, 1 H); 3.70 (d, J=12.0 Hz, 1 H); 3.89 (s, 3 H); 4.59 (d, J=6.4 Hz, 1 H); 6.06 (d, J=8 Hz, 1 H).

Example 12

(2S,3S,4S,5R,6S)-3,4,5-trihydroxy-6-(3-methyl-1-(1-propylpiperidin-2-yl)-6,7,8,9-tetrahydro-3H-pyrazolo[3,4-c]isoquinoline-5-oxy)tetrahydro-2H-pyran-2-formic Acid The compound of Example 12 was prepared with similar experimental procedures and methods to those in Example 11 except that the aldehyde in Example 11F was replaced with propanal. MS (ESI): m/z 505 (M+1, 100%); $^1$H NMR (400 MHz, CD$_3$OD): δ 0.67-0.70 (m, 3 H); 1.44-1.68 (m, 4 H); 1.72-1.79 (m, 4 H); 1.84-2.00 (m, 6 H); 2.57-2.69 (m, 2 H); 2.74-2.92 (m, 3 H); 3.01-3.11 (m, 2 H); 3.38-3.57 (m, 4 H); 3.61-3.73 (m, 2 H); 3.89 (s, 3 H); 4.58-4.63 (m, 1 H), 6.07 (d, J=6.8 Hz, 1 H)

Example 13

(2S,3S,4S,5R,6S)-3,4,5-trihydroxy-6-(3-methyl-1-(1-propylpiperidin-3-yl)-6,7,8,9-tetrahydro-3H-pyrazolo[3,4-c]isoquinoline-5-oxy)tetrahydro-2H-pyran-2-formic Acid The compound of Example 13 was prepared with similar experimental procedures and methods to those in Example 11 except that Cbz-R-proline in Example 4A was replaced with Cbz-3-piperidine carboxylic acid. MS (ESI): m/z 505 (M+1, 100%); $^1$H NMR (400 MHz, D$_2$O): δ 0.79-0.84 (m, 3 H); 1.33 (d, J=6.4 Hz, 1 H); 1.57-1.62 (m, 7 H); 1.82-1.94 (m, 2 H); 1.95-2.01 (m, 1 H); 2.37-2.46 (m, 2 H); 2.49-2.52 (m, 1 H); 2.71-3.05 (m, 7 H); 3.44-3.49 (m, 2 H); 3.52 (s, 1 H); 3.53-3.59 (m, 2 H); 3.65 (s, 1 H); 3.70 (s, 3 H); 3.78-3.83 (m, 1 H); 5.94-5.99 (m, 1 H)

Example 14

(2S,3S,4S,5R,6S)-3,4,5-trihydroxy-6-(3-methyl-1-(1-propylpiperidin-4-yl)-6,7,8,9-tetrahydro-3H-pyrazolo[3,4-c]isoquinoline-5-oxy)tetrahydro-2H-pyran-2-formic Acid The compound of Example 14 was prepared with similar experimental procedures and methods to those in Example 4 except that Cbz-R-proline in Example 4A was replaced with Cbz-4-piperidine carboxylic acid. MS (ESI): m/z 505 (M+1, 100%); $^1$H NMR (400 MHz, CD$_3$OD): δ 0.93 (t, J=7.4 Hz, 3 H); 1.17-1.35 (m, 2 H); 1.64-1.84 (m, 7 H); 1.89-1.95 (m, 1 H); 2.10-2.24 (m, 1 H); 2.45-2.51 (m, 1 H); 2.69-3.11 (m, 9 H); 3.36-3.53 (m, 5 H); 3.61-3.64 (m, 1 H); 3.72 (s, 3 H); 3.80 (d, J=9.6 Hz, 1 H); 6.02 (d, J=7.6 Hz, 1 H)

Example 15

(2S,3S,4S,5R,6S)-3,4,5-trihydroxy-6-(3-methyl-1-(1-propylpyrrolidin-3-yl)-3,6,7,8-tetrahydrocyclopentano[d]pyrazolo[3,4-b]pyridine-5-oxy)tetrahydro-2H-pyran-2-formic Acid The compound of Example 15 was prepared with similar experimental procedures and methods to those in Example 4 except that cyclohexanone in Example 4D was replaced with cyclopentanone. MS (ESI): m/z 477 (M+1, 100%); $^1$H NMR (400 MHz, D$_2$O): δ 0.69-0.76 (m, 3 H); 1.45-1.56 (m, 2 H); 1.81-1.95 (m, 3 H); 2.07-2.39 (m, 2 H); 2.48-2.59 (m, 2 H); 2.64-2.88 (m, 2 H); 2.90-2.92 (m, 1 H); 2.96-3.09 (m, 3 H); 3.16-3.24 (m, 2 H); 3.38-3.44 (m, 3 H); 3.56 (s, 3 H), 3.73-3.75 (m, 1 H); 5.83-5.86 (m, 1 H)

Example 16

(2S,3S,4S,5R,6S)-3,4,5-trihydroxy-6-(3-methyl-1-(1-propylpyrrolidin-3-yl)-3H-pyrazolo[3,4-c]isoquinoline-5-oxy)tetrahydro-2H-pyran-2-formic Acid Example 16A 3-methyl-1-(1-propylpyrrolidin-3-yl)-3H-pyrazolo[3,4-c]isoquinoline-5(4H)-one The compound of Example 16A was prepared according to the process as shown in the Reaction Scheme 1 and the specific experimental conditions in U.S. Pat. No. 7,501,412.

(2S,3S,4S,5R,6S)-3,4,5-trihydroxy-6-(3-methyl-1-(1-propylpyrrolidin-3-yl)-3H-pyrazolo[3,4-c]isoquinoline-5-oxy)tetrahydro-2H-pyran-2-formic Acid The compound of Example 16 was prepared with similar experimental procedures and methods to those in Example 4 except that the compound 4G in Example 4H was replaced with Example 16A.

Example 17

(2S,3S,4S,5R,6S)-3,4,5-trihydroxy-6-(3-methyl-1-(1-cyclopentylpyrrolidin-3-yl)-6,7,8,9-tetrahydro-3H-pyrazolo[3,4-c]isoquinoline-5-oxy)tetrahydro-2H-pyran-2-formic Acid Example 17A 1-(1-cyclopentyl-3-pyrrolyl)-3-methyl-6,7,8,9-tetrahydropyrazolo[3,4-c]isoquinoline-5-one Under nitrogen atmosphere, to a 250 mL of reaction flask were added the compound of Example 7A (0.5 g, 1.84 mmol), cyclopentanone (0.46 g, 5.51 mmol), zinc chloride (0.5 g, 3.67 mmol) and methanol (100 mL). The mixture was stirred for 2 hr at room temperature. Sodium cyanoborohydride (0.35 g, 5.51 mmol) was added to the mixture and stirred overnight. After the reaction completed, the product was concentrated to remove methanol and purified with preparative silica gel to give 500.4 mg of the title compound as white solid. Yield: 80.0%. MS (ESI): m/z 341 (M+1, 100%)

(2S,3S,4S,5R,6S)-3,4,5-trihydroxy-6-(3-methyl-1-(1-cyclopentylpyrrolidin-3-yl)-6,7,8,9-tetrahydro-3H-pyrazolo[3,4-c]isoquinoline-5-oxy)tetrahydro-2H-pyran-2-formic Acid The compound of Example 17 was prepared with similar experimental procedures and methods to those in Examples 4H and 4 except that the starting material Example 4G in Example 4H was replaced with Example 17A. MS (ESI): m/z 517 (M+1, 100%); $^1$H NMR (400 MHz, CD$_3$OD): δ 1.71-1.73 (m, 5 H); 1.82-1.85 (m, 8 H); 2.13-2.20 (m, 3 H); 2.24-2.31 (m, 2 H); 2.43-2.52 (m, 2 H); 2.65-2.75 (m, 4 H); 2.96-3.05 (m, 3 H); 3.55-3.59 (m, 3 H); 3.87-3.88 (m, 1 H); 4.10 (s, 3 H); 6.14 (d, J=7.2 Hz, 1 H)

Example 18

(2S,3S,4S,5R,6S)-3,4,5-trihydroxy-6-(3-methyl-1-(R)-1-isopropylpyrrolidin-2-yl)-6,7,8,9-tetrahydro-3H-pyrazolo[3,4-c]isoquinoline-5-oxy)tetrahydro-2H-pyran-2-formic Acid The compound of Example 18 was prepared with similar experimental procedures and methods to those in Example 4 except that propanal in Example 4G was replaced with acetone. MS (ESI): m/z 471 (M−3, 100%); $^1$H NMR (400 MHz, CD$_3$OD): δ 1.31 (d, J=6.4 Hz, 6 H); 1.82-1.94 (m, 5 H); 2.05-2.22 (m, 3 H); 2.61-2.77 (m, 4 H); 3.06-3.13 (m, 3 H); 3.33-3.38 (m, 1 H); 3.54-3.63 (m, 3 H); 3.67-3.72 (m, 2 H); 3.80 (d, J=8.8 Hz, 1 H); 3.98 (s, 3 H); 5.13-5.16 (m, 1 H); 6.15 (d, J=8.0 Hz, 1 H)

Example 19

To evaluate the inhibition activities in vitro, especially in vivo of the compounds of the present application against PARP, the inhibition effects of the compounds of the present application against PAR formation in mouse tumors were determined by the following Elisa assays in accordance with the process reported by Xuesong Liu, et al, *Analytical Biochemistry*, Vol 381, p240-247 (2008).

PAR ELISA Assay

Chemical Reagents and Antibodies

All the chemical reagents used were commercially available analytical pure chemicals. The reagents were purchased from different chemical corporations. The reagents were not purified prior to use except specifically indicated.

The following reagents and antibodies were purchased from Trevigen Corporation, USA: PAR standard substance (Lot No. 4336-100-01), monoclonal antibody of anti-PAR (Lot No. cat.4335-MC-100), polyclonal antibody of Anti-PAR (Lot No. cat.4336-BPC-100), cell lysis solution (Lot No. FNN0011).

HRP bonded goat antirabbit antibodies were purchased from KPL Corporation, USA (Lot No. 074-1506).

ELISA chemiluminescent substrates were products of Thermo Corporation USA (Lot No. 37070).

Bovine serum albumin (BSA) and proteinase inhibitors were purchased from Sigma Corporation (Lot No. Sigma A-4503) and Amresco Corporation (Lot No. M221), respectively.

BCA protein quantitative assay kits were purchased from China Jiangsu Beyotime Biotechnology Limited (Lot No: P0012).

All the purchased chemicals and biological reagents were strictly stored according to the specifications for later use.
Preparation of Reagents Carbonate buffer: 8.4 g of NaHCO$_3$, 3.56 g of Na$_2$CO$_3$ were weighed and quantified to 1 L with distilled water. pH was adjusted with HCl to 9.6.

0.01 M standard PBS solution: 7.9 g of NaCl, 0.2 g of KCl, 1.44 g of Na$_2$HPO$_4$.12H$_2$O and 1.8 g of K$_2$HPO$_4$ were weighed and dissolved in 800 mL of distilled water. pH was adjusted with HCl to 7.4. The solution was quantified to 1 L with distilled water.

100× proteinase inhibitors: 1 mL of deionized water was added to freeze-dried proteinase inhibitor powder in EP tube. The mixture was shaken for 1 min and centrifuged for 30 sec.

Cell Lysis Buffer: 1 mL of solution comprises 985 μL of Cell Extraction Buffer, 5 μL of 200 mM PMSF and 10 μL of 100× proteinase inhibitors.

PBS cleansing solution: 100 μL of Tween-20 was taken and quantified to 100 mL with standard PBS solution.

PBS confining liquid: 2 g of BSA powder (Sigma) was taken and quantified to 100 mL with standard PBS solution.

PBS diluent: 2 g of BSA powder (Sigma) and 0.5 g of SDS powder were taken and quantified to 100 mL with standard PBS solution.

0.9% NaCl standard diluent: 0.9 g of NaCl powder were weighed and dissolved in 100 mL of distilled water.

Protein standard solution: 0.8 mL of protein standard preparation solution was taken. 20 mg of BCA protein assay kit protein standard (BSA) were added to prepare as protein standard solution A with concentration of 25 mg/mL. The protein standard solution A was stored at −20° C. When use, 20 μL of protein standard solution A and 980 μL of diluted solution of the standard substance were taken to prepare 0.5 mg/mL of protein standard solution B.

BCA working solution: 5 mL of BCA reagent A and 100 μL of BCA reagent B were taken to prepare 5.1 mL of BCA working solution.
PAR ELISA Assay The anti-PAR monoclonal antibodies were diluted 500 folds with 0.1 M of carbonic acid buffer. The diluted antibodies were added to enzyme labelling 96-well plates at 100 μL per well, and encapsulated for 2 hr at 37° C. The liquid in the wells was discarded. The residual liquid was absorbed by gently tapping on paper towel. PBS cleansing solution (about 250 μL per well) was added. Each well was washed 5 times for 3 to 5 min. 250 μL of PBS confining liquid were added in each well. The wells were covered with membrane and incubated for 1 hr at 25° C. The confining liquid was removed and absorbed by absorbent paper. 75 μL of a series of diluted standard solution of PAR or extracts to be tested were added in each well. Three wells constitute a group. Each well was covered with membrane and incubated overnight at 4° C. Then the membrane was removed and each well was washed five times with 250 μL of PBS cleansing solution. Each washing lasted for 3-5 min. To completely remove the liquid in the wells, the liquid was removed with absorbent paper. The anti-PAR polyclonal antibodies were diluted 500 folds with PBS confining liquid. 100 μL of diluted PAR secondary antibodies were added. Each well was covered with membrane and incubated for 2 hr at room temperature. The plate was vortexed to mix homogeneously. The membrane was removed. Each well was washed five times with 250 μL of PBS cleansing. Each washing lasted for 3-5 min. The goat antirabbit IgG-HRP bonded antibodies (tertiary antibody)

were diluted with PBS blocking solution to 2 g/mL of enzyme labelling antibodies. 100 μL of freshly prepared enzyme labelling antibodies were added in each well. The well was sealed with membrane and incubated for 1 hr at room temperature. The plate was vortexed to mix homogeneously. After the membrane was removed, the well was washed five times with PBS cleansing solution. Each washing lasted for 3-5 min. The chemiluminescent substrates A and B were mixed with the same volume. The mixture was used as HPR substrate luminescent agents. Immediately after adding 100 μL of the mixture in each well, the combined light numbers were read by SpectraMax M5 (relative to light unit).

Acquisition of Tumor Biopsy Tissues and Extraction of Proteins in Tissues 50 mg of tumor biopsy samples were collected and transferred to 1.5 mL of centrifuge tube. 500 μL of frozen cell lysate comprising 1× protein inhibitors and 1 mM of PMSF were added in the tube on ice The mixture was sufficiently and homogeneously triturated, mixed for 30 sec by high speed vortex and ultrasonic treated for 30 sec by ultrasonic pyrolyzer with power of 2-3 W, and repeated 3 times. The product was centrifuged for 15 min under 13,000 rpm with refrigeration centrifuge at 4° C. SDS was added into supernate such that the final concentration of SDS was 1%. The sample was shaken for 10 sec, and then boiled for 5 min in 100° C. boiling water. The boiled sample was vortexed and shaken with high speed for 10 sec in test tube cooled with brash ice. The product was centrifuged for 5-10 min under 13,000×g at 4° C. The solution was clarified. The supernate was used as the extracted protein solution.

BCA Protein Assays

The protein concentration of the extract was determined by BCA process: 20 mg of BCA protein assay kit protein standard (BSA) was added to 0.8 mL of protein standard preparation to prepare 25 mg/mL of protein standard solution A. 20 μL of protein standard solution A and 980 μL of 0.9% NaCl solution were used to prepared 0.5 mg/mL of protein solution B. 5 mL of BCA standard solution A and 100 μL of BCA reagent B were used to prepare 5.1 mL, of BCA working solution. The protein standard solution B was added in standard material well of a 96-well plate at 0, 1, 2, 4, 8, 12, 16, 20 μL, respectively. 20 μL with 0.9% NaCl diluent were supplemented. Each sample was added in sample material well of the 96-well plate. 20 μL were added for each well. Each sample was added in three wells. 200 μL of BCA working solution were added in each well. The plate was kept for 20-30 min at 37° C. A562 was determined. The protein concentrations of the samples were calculated according to the standard curve.

Preparation of PAR Standard Curves

PAR standard solution (Trevigen Corporation, 4336-100-01) was used to prepare standard solutions with concentrations of 1200 pg/mL, 600 pg/mL, 300 pg/mL, 150 pg/mL, 75 pg/mL, 37.5 pg/mL and 18.75 pg/mL, with PBS standard solutions. The volume of each standard solution is 250 μL. The chemiluminescence was determined according ELISA assay process for PAR contents. The standard curve was plotted.

Tumor Inoculation Tests in Mice

Establishment of C57BL/6 Bearing Tumor Mice

The revived B16F10 melanoma cell strains (KeyGen Biotech Limited, Nanjing) were cultured with RPMI-1640 culture solution comprising 10% of bovine serum, 0.25 mM of Hepes, 100 U/mL of penicillin and 100 μg/mL of streptomycin in an incubator having 5% $CO_2$ at 37° C. The cells in exponentially proliferation were digested with 0.25% of pancreatin and collected in serum-free petri dishes, and then gently shaken. The viability of the assay cells such as trypan blue stain was over 95% according to counting the cell suspension.

SPF (specific pathogen free) grade closed colony inbred strain C57BL/6 female mice (Shanghai Sippr BK Laboratory Animals Ltd), each of which was 6-8 weeks old and had weight of about 20 g. The belly skin of each one was sterilized with 75% alcohol, and the above B16F10 melanoma cells solution was subcutaneously inoculated into left front ribs of the mice. Each one was inoculated in combination of $3.6 \times 10^6$ cells and matrigel at ratio of 1:1. The administration started when the size of the tumor grown to about 500 $mm^3$.

Establishment of MX-1 BALB/c Nude Mice and Bearing Tumor Mice

The revived MX-1 human breast cancer cell strains (KeyGen Biotech Limited, Nanjing) was cultured with RPMI-1640 culture solution comprising 10% of bovine serum, 1% (w/v) of penicillin and 1% (w/v) of streptomycin in an incubator having 5% $CO_2$ at 37° C. Passage amplification was carried out. The cells in exponentially proliferation were collected and blown with blowpipe, and then collected in free-bovine incomplete culture solution, and gently shaken to prepare cell suspension. The cells were counted and the viability of cell is over 95% according to typan blue stain assay.

SPF grade Balb/c female nude mice (Shanghai Sippr BK Laboratory Animals Ltd) which were 4-6 weeks old and had weight of 18-22 g, were sterilized with 75% alcohol and then inoculated left lower limbs groin. Each one was inoculated in combination of $2 \times 10^6$ cells and matrigel at ratio of 1:1. The administration started when the size of the tumor grown to about 500 $mm^3$.

Drug Administration

Preparation of control group: To a 100 mL of volumetric flask were added 5 mL of ethanol and 25 mL of PEG400. The mixture was quantified with PBS preparation solution comprising 0.05% of TW 80 (one drop was added in 100 mL) and shaken. The resultant solution was stored at room temperature for later use. Gastric lavage dosage for each mouse was 0.2 mL. When the size of the tumor reached 500 $mm^3$, the tumor bearing mice were administered twice per day for continuous 5 days. Then the tumors were subject to biopsy.

Compound dosing group: The above preparations were used to prepare 1.25 mg/mL of sample. Gastric lavage dosage for each mouse was 0.2 mL. When the size of the tumor reached 500 $mm^3$, the bearing cancer mice were administered twice per day for continuous 5 days. Then the tumors were subject to biopsy.

PAR Inhibitory Effects of Compounds of Present Application in Tumor-Bearing Mice According to the ELISA experiment described above, the PAR concentration of each test sample was calculated through comparison to the standard curve. The obtained values were then compared to control experiments, so as to obtain inhibitory effects of the compounds of the present application on PAR formation, indicating the in vivo inhibitory effect of PARP activity.

1. Inhibition effects on the PARP activity in tumors of C57BL/6 tumor bearing mice inoculated with B16F10 melanoma cell line:

The following compounds showed equal or higher than 80% inhibition against PARP in vivo when administered as above.

| 2 | 4 | 9 | 10 | 12 | 18 | 19 |

The following compounds showed equal or higher than 60% but less than 80% inhibition against PARP in vivo when administered as above.

| 1 | 3 | 5 | 6 | 7 | 8 | 11 | 13 | 14 | 15 |

2. The PARP inhibitory effects in tumors of Balb/c nude mice inoculated with MX-1 human breast cancer cell line:

The following compounds showed equal or higher than 90% inhibition against PARP in vivo when administered as above.

| 9 | 10 | 18 | 19 |

The following compounds showed equal or higher than 80% but less than 90% inhibition against PARP in vivo when administered as above.

| 1 | 2 | 3 | 4 | 5 | 8 | 11 | 12 |

The following compounds showed equal or higher than 70% but less than 80% inhibition against PARP in vivo when administered as above.

| 6 | 7 | 9 | 10 | 13 | 14 | 15 |

From the foregoing it will be appreciated that, although specific embodiments of the present application have been described herein for purpose of illustration, various modifications or improvements may be made by a person having ordinary skill in the art without deviating from the spirit and scope of the present application. These modifications and improvements should fall within the scope of the appended claims in the present application.

What is claimed is:

1. A compound of general formula (I) or a pharmaceutically acceptable salt thereof:

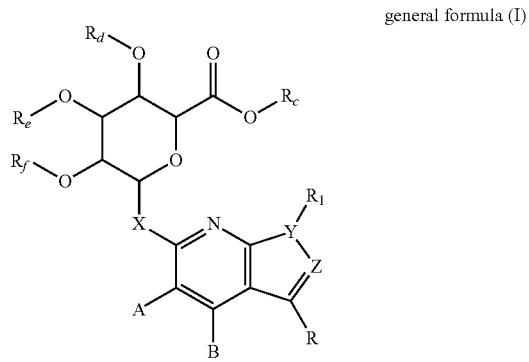

general formula (I)

wherein:

A and B together with carbons to which A and B attach represent optionally substituted $C_{6-10}$ aryl, or optionally substituted $C_{3-10}$ cyclohydrocarbyl;

$R_c, R_d, R_e$ and $R_f$ are independently selected from hydrogen, optionally substituted $C_{1-6}$ alkyl and optionally substituted $C_{1-6}$ acyl;

$R_1$ is independently selected from the group consisting of hydrogen, optionally substituted $C_{1-6}$ alkyl and optionally substituted $C_{1-6}$ haloalkyl;

R is independently selected from the group consisting of hydrogen, optionally substituted $C_{1-6}$ alkyl, optionally substituted $C_{1-6}$ haloalkyl, $C_{3-18}$ heterocyclyl optionally substituted with $C_{1-6}$ alkyl or $C_{1-6}$ haloalkyl or $C_{3-12}$ cycloalkyl, optionally substituted $C_{6-10}$ aryl, and optionally substituted $C_{7-16}$ arylalkyl, wherein the heteroatom is selected from the group consisting of nitrogen, oxygen and sulphur; and X represents oxygen or sulphur;

Y and Z are independently selected from the group consisting of nitrogen, oxygen, sulphur and optionally substituted methylene, provided that when Y is oxygen or sulphur, then $R_1$ is absent.

2. The compound of claim 1, wherein X is oxygen.

3. The compound of claim 1, wherein Y and Z are each nitrogen.

4. The compound of claim 1, wherein $R_c$, $R_d$, $R_e$ and $R_f$ are independently selected from hydrogen and optionally substituted $C_{1-6}$ alkyl.

5. The compound of claim 1, wherein A and B together with carbons to which A and B attach represent phenyl, cyclopentyl or cyclohexyl.

6. The compound of claim 1, wherein R is selected from the group consisting of $C_{1-6}$ alkyl, phenyl, $C_{1-6}$ alkylpyrrolidinyl, $C_{1-6}$ haloalkylpyrrolidinyl, $C_{1-6}$ cycloalkyl pyrrolidinyl and $C_{1-6}$ alkylpiperidyl.

7. The compound of claim 1, which is selected from the group consisting of (2S,3S,4S,5R,6S)-6-(1,3-dimethyl-6,7,8,9-tetrahydro-3H-pyrazolo[3,4-c]isoquinoline-5-oxy)-3,4,5-trihydroxytetrahydro-2H-pyran-2-formic acid;

(2S,3S,4S,5R,6S)-3,4,5-trihydroxy-6-(1-isopropyl-3-methyl-6,7,8,9-tetrahydro-3H-pyrazolo[3,4-c]isoquinoline-5-oxy)-tetrahydro-2H-pyran-2-formic acid;

(2S,3S,4S,5R,6S)-3,4,5-trihydroxy-6-(1-phenyl-3-methyl-6,7,8,9-tetrahydro-3H-pyrazolo[3,4-c]isoquinoline-5-oxy)-tetrahydro-2H-pyran-2-formic acid;

(2S,3S,4S,5R,6S)-3,4,5-trihydroxy-6-(3-methyl-1-((R)-1-propylpyrrolidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-((S)-1-propylpyrrolidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-ethylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-(3,3,3-trifluoropropyl)pyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-((R)-1-propylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-((S)-1-propylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(1-(1-ethylpiperidin-2-yl)-3-methyl-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpiperidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3  -methyl-1-(1-propylpiperidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpiperidin-4-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-propylpyrrolidin-3-yl)-3,6,7,8-tetrahydrocyclopentano[d]pyrazolo[3,4-b]pyridine-5-oxy)tetrahydro-2H-pyran-2-formic acid;

(2S,3S,4S,5R,6S)-3,4,5-trihydroxy-6-(3-methyl-1-(1-propylpyrrolidin-3-yl)-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(1-cyclopentylpyrrolidin-3-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-trihydroxy-6-(3-methyl-1-(R)-1-isopropylpyrrolidin-2-yl)-6,7,8,9-tetrahydro-3H-pyrazolo[3,4-c]isoquinoline-5-oxy)tetrahydro-2H-pyran-2-formic acid;

(2S,3S,4S,5R,6S)-3,4,5-triacetyl-6-(1,3-dimethyl-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(1-isopropyl-3-methyl-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(3-methyl-1-phenyl-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(3-methyl-1-((R)-1-propylpyrrolidin-2-yl)-6,7,8 ,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-((S)-1-propylpyrrolidin-2-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpyrrolidin-3-yl)-6,7,8,9-tetrahydro-3 H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-ethylpyrrolidin-3-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-(3,3,3-trifluoropropyl)pyrrolidin-3-yl)-6,7,8,9-tetrahydro-3 H-pyrazolo[3,4-c]isoquinoline-5-oxy)tetrahydro-2H-pyran-2-methylformate;

(2S,3S,4S,5R,6S)-3,4,5-triacetyl-6-(3-methyl-1-((R)-1-propylpyrrolidin-3-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-triacetyl-6-(3-methyl-1-((S)-1-propylpyrrolidin-3 -yl)-6,7,8,9-tetrahydro-3H-pyrazolo[3,4-c]isoquinoline-5-oxy)-tetrahydro-2H-pyran-2-methylformate;

(2S,3S,4S,5R,6S)-3,4,5-triacetyl-6-(1-(1-ethylpiperidin-2-yl)-3-methyl-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpiperidin-2-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpiperidin-3-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpiperidin-4-yl)-6,7,8,9-tetrahydro-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-propylpyrrolidin-3-yl)-3,6,7,8-tetrahydrocyclopentano[d]pyrazolo[3,4-b]pyridine-5-oxy)tetrahydro-2H-pyran-2-methylformate;

(2S,3S,4S,5R,6S)-3,4,5-trihydroxy-6-(3-methyl-1-(1-propylpyrrolidin-3-yl)-3H-pyrazolo[3,4-c]isoquinoline-5-oxy)tetrahydro-2H-pyran-2-methylformate;

(2S,3S,4S,5R,6S)-3,4,5-trihydroxy-6-(3-methyl-1-(1-cyclopentylpyrrolidin-3-yl)-6,7,8,9-tetrahydro-3H-pyrazolo[3,4-c]isoquinoline-5-oxy)tetrahydro-2H-pyran-2-methylformate; and (2S,3S,4S,5R,6S)-3,4,5-trihydroxy-6-(3-methyl-1-(R)-1-isopropylpyrrolidin-2-yl)-6,7,8,9-tetrahydro-3H-pyrazolo[3,4-c]isoquinoline-5-oxy)tetrahydro-2H-pyran-2-methylformate.

8. A process for preparing a compound of claim 1, comprising reacting a compound of general formula (XIV) with a compound of general formula (XVI) to obtain a compound of general formula (I),

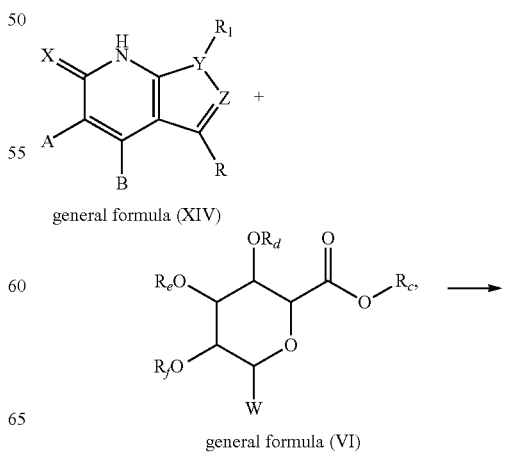

general formula (XIV)

general formula (VI)

-continued

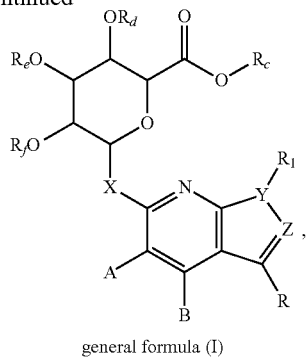

general formula (I)

wherein, W is halogen, and A, B, X, Y, Z, R, $R_1$, $R_c$, $R_d$, $R_e$ and $R_f$ are as defined in claim 1.

9. The method of claim 8, further comprising wherein the compound of general formula (XIV) reacts with the compound of general formula (VI) in the presence of a base.

10. A pharmaceutical composition, comprising a pharmaceutically acceptable carrier and a therapeutically effective amount of a compound of claim 1.

11. The pharmaceutical composition of claim 10, further comprising an additional active ingredient.

12. The pharmaceutical composition of claim 11, wherein the additional active ingredient is selected from the group consisting of nitrogen mustard, aziridine, methylmelamine, alkyl sulphonate, nitrosourea, triazene, folacin, vinca alkaloid, epipodophyllotoxin, acivicin, aclarubicin, hydrochloride acodazole, acronine, adozelesin, aldesleukin, ambomycin, ametantrone acetate, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin, droloxifene hydrochloride, epirubicin hydrochloride, esorubicin hydrochloride, estramustine, etanidazole, etoposide, floxuridine, fluorouracil, flurocitabine gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, camptothecin, hexadecadrol, aspirin, acetaminophen, indometacin, ibuprofen, ketoprofen, meloxicam, corticosteroid and adrenal corticosteroid.

13. A method for treating a disease or condition mediated by poly(ADP-ribose) polymerase (PARP), comprising administering a subject in need thereof a therapeutically effective amount of a compound of claim 1, wherein the disease or condition is breast cancer or malignant melanoma.

14. The method of claim 13, wherein a compound is administered a unit dose of 0.1 mg-1,000 mg.

15. The method of claim 13, further comprising administering to the subject an additional active ingredient.

16. The method of claim 15, wherein the additional active ingredient is selected from the group consisting of nitrogen mustard, aziridine, methylmelamine, alkyl sulphonate, nitrosourea, triazene, folacin, vinca alkaloid, epipodophyllotoxin, acivicin, aclarubicin, hydrochloride, acodazole, acronine, adozelesin, aldesleukin, ambomycin, ametantrone acetate, aminoglutethimide, amsacrine, anastrozole, antramycin, asparaginasum, azithromycin, azacitidine, azetepa, azotomycin, batimastat, benzodepa, bicalutamide, bisantrene hydrochloride, bisnafide mesilate, bizelesin, bleomycin sulfate, busulfan, actinomycin C, calusterone, caracemide, carbetimer, carboplatin, carmustine, carubicin hydrochloride, chlorambucil, cirolemycin, cladribine, crisnatol mesilate, cyclophosphamide, cytarabine, dacarbazine, actinomycin D, daunorubicin hydrochloride, decitabine, docetaxel, doxorubicin, doxorubicin, droloxifene hydrochloride, epirubicin hydrochloride, esorubicin hydrochloride, estramustine, etanidazole, etoposide, floxuridine, fluorouracil, flurocitabine, gemcitabine, idarubicin hydrochloride, ifosfamide, interleukin II, interferon α-2a, interferon α-2b, irinotecan hydrochloride, letrozole, mercaptopurine, methotrexate, metropine, mitomycin, mitoxantrone, paclitaxel, procarbazine, thiotepa, vinblastine, vincristine, camptothecin, hexadecadrol, aspirin, acetaminophen, indometacin, ibuprofen, ketoprofen, meloxicam, corticosteroid and adrenal corticosteroid.

17. The method of claim 16, wherein the therapeutically effective amount of a compound and the additional active ingredient are simultaneously, synergistically, separately or sequentially administered to the subject.

* * * * *